United States Patent
Thomas et al.

(10) Patent No.: US 7,510,758 B2
(45) Date of Patent: Mar. 31, 2009

(54) BREATHABLE ELASTIC MULTILAYER FILM LAMINATE AND METHOD OF MAKING A BREATHABLE ELASTIC MULTILAYER FILM LAMINATE

(75) Inventors: Oomman Painumoottil Thomas, Alpharetta, GA (US); Vasily Aramovich Topolkaraev, Appleton, WI (US); Stephen Clark Smith, Atlanta, GA (US); Susan Elaine Shawver, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 481 days.

(21) Appl. No.: 10/293,253

(22) Filed: Nov. 12, 2002

(65) Prior Publication Data

US 2004/0091693 A1 May 13, 2004

(51) Int. Cl.
*B32B 27/08* (2006.01)
*A61F 13/15* (2006.01)

(52) U.S. Cl. .......... 428/198; 428/317.9; 428/319.3; 428/319.7; 428/316.6; 428/152; 428/156; 428/166; 428/167; 428/181

(58) Field of Classification Search .......... 428/317.9, 428/319.3, 319.7, 316.6, 317.1, 198, 152, 428/156, 166, 167, 181; 525/64, 66, 69; 524/442
See application file for complete search history.

(56) References Cited

U.S. PATENT DOCUMENTS

| | | | |
|---|---|---|---|
| 3,836,423 A | 9/1974 | Wagner et al. | |
| 3,844,865 A | 10/1974 | Elton et al. | |
| 4,613,643 A | 9/1986 | Nakamura et al. | |
| 4,623,587 A | 11/1986 | Ito et al. | |
| 4,725,481 A * | 2/1988 | Ostapchenko | 428/213 |
| 4,758,462 A | 7/1988 | Park et al. | |
| 4,874,568 A | 10/1989 | Chau et al. | |
| 4,878,974 A | 11/1989 | Kagawa | |
| 5,208,098 A | 5/1993 | Stover | |
| 5,244,716 A | 9/1993 | Thornton et al. | |
| 5,269,995 A | 12/1993 | Ramanathan et al. | |

(Continued)

FOREIGN PATENT DOCUMENTS

EP 611 738 8/1994

(Continued)

OTHER PUBLICATIONS

A.L. Volynskii, S. Bazhenov, O.V. Lebedeva and N. F. Bakeev: *Mechanical Buckling Instability of Thin Coatings Deposited on Soft Polymer Substrates*, Journal of Materials Science 35, pp. 547-554, Kluwer Academic Publishers. (2000).

(Continued)

*Primary Examiner*—Hai Vo
(74) *Attorney, Agent, or Firm*—Dority & Manning, P.A.

(57) ABSTRACT

A breathable, elastic, film laminate including layers of an inherently breathable, elastic polymer film alternately stacked with layers of a filled plastic polymer. The laminate may be made by grafting a thermoplastic polymer to an elastomer to form an inherently breathable elastic polymer, extruding, the elastic polymer through a die, extruding the filled plastic polymer through a die, stacking the extruded elastic polymer with the extruded plastic polymer while the polymers are in a melt-extrudable state to create a multilayer film laminate, and stretching the laminate.

27 Claims, 7 Drawing Sheets

U.S. PATENT DOCUMENTS

| | | | |
|---|---|---|---|
| 5,272,236 A | 12/1993 | Lai et al. | |
| 5,278,272 A | 1/1994 | Lai et al. | |
| 5,331,047 A | 7/1994 | Giacobbe | |
| 5,372,882 A | 12/1994 | Peiffer et al. | |
| 5,376,430 A | 12/1994 | Swenson et al. | |
| 5,397,635 A | 3/1995 | Wood, Jr. | |
| 5,445,862 A | 8/1995 | Kaneko et al. | |
| 5,571,619 A | 11/1996 | McAlpin et al. | |
| 5,616,420 A | 4/1997 | Yamaoka et al. | |
| 5,695,868 A | 12/1997 | McCormack | |
| 5,840,812 A | 11/1998 | Schultze | |
| 5,843,056 A * | 12/1998 | Good et al. | 604/367 |
| 5,869,414 A | 2/1999 | Fischer et al. | |
| 5,908,690 A | 6/1999 | Schultze et al. | |
| 5,914,184 A * | 6/1999 | Morman | 428/315.9 |
| 5,932,497 A | 8/1999 | Morman et al. | |
| 5,955,187 A * | 9/1999 | McCormack et al. | 428/315.5 |
| 5,993,589 A | 11/1999 | Morman | |
| 6,001,464 A | 12/1999 | Schultze et al. | |
| 6,002,064 A | 12/1999 | Kobylivker et al. | |
| 6,045,895 A | 4/2000 | Hyde et al. | |
| 6,045,900 A | 4/2000 | Haffner et al. | |
| 6,071,450 A | 6/2000 | Topolkaraev et al. | |
| 6,072,005 A | 6/2000 | Kobylivker et al. | |
| 6,075,179 A | 6/2000 | McCormack et al. | |
| 6,114,024 A | 9/2000 | Forte | |
| 6,117,438 A | 9/2000 | Topolkaraev et al. | |
| 6,139,675 A | 10/2000 | Druecke et al. | |
| 6,156,421 A | 12/2000 | Stopper et al. | |
| 6,245,401 B1 | 6/2001 | Ying et al. | |
| 6,261,674 B1 | 7/2001 | Branham et al. | |
| 6,479,154 B1 | 11/2002 | Walton et al. | |
| 6,677,258 B2 * | 1/2004 | Carroll et al. | 442/394 |
| 6,828,019 B2 * | 12/2004 | Kong et al. | 428/354 |
| 6,984,439 B2 * | 1/2006 | Topolkaraev | 428/182 |
| 7,179,952 B2 * | 2/2007 | Vukos et al. | 604/378 |
| 2004/0170852 A1 * | 9/2004 | Gustafson | |

FOREIGN PATENT DOCUMENTS

| | | |
|---|---|---|
| EP | 963 837 | 12/1999 |
| EP | 979 838 | 2/2000 |
| JP | 01288439 | 11/1989 |
| JP | 03193343 | 8/1991 |
| JP | 03193344 | 8/1991 |
| JP | 03254938 | 11/1991 |
| WO | 98/23673 | 6/1998 |
| WO | 99/33654 | 7/1999 |
| WO | 00/13889 | 3/2000 |
| WO | 01/28769 | 4/2001 |
| WO | WO 01/32403 A1 | 5/2001 |
| WO | WO 0183210 A1 * | 11/2001 |

OTHER PUBLICATIONS

Cellular Materials to Composites, *Encyclopedia of Polymer Science and Engineering*, vol. 3, pp. 299-300, (1985), John Wiley & Sons.

W. J. Schrenk and T. Alfrey, Jr.: Coextruded Multilayer Polymer Films and Sheets, *Polymer Blends*, vol. 2, pp. 129-165, Academic Press, Inc. (1978).

\* cited by examiner

BREATHABLE ELASTIC MULTILAYER FILM LAMINATE AND METHOD OF MAKING A BREATHABLE ELASTIC MULTILAYER FILM LAMINATE

BACKGROUND OF THE INVENTION

The present invention is directed to breathable elastic multilayer film laminates having alternating layers of elastic and plastic polymers, and methods of making such laminates.

Films are typically used to provide barrier properties in absorbent articles. More specifically, absorbent materials are incorporated into absorbent articles to absorb bodily fluids or other liquids, and films are incorporated into absorbent articles to prevent the absorbed fluids and any excess fluids from transferring onto a wearer's clothing or migrating into other undesirable areas. Films are also used to provide barrier properties in other types of disposable items, such as surgical and health care related products, as well as in disposable work wear such as coveralls and lab coats. In these types of protective apparel, films are used to prevent cross exchange of microorganisms through the protective apparel.

Ideal films for absorbent articles and other disposable items are liquid-impermeable yet vapor-permeable, thereby providing a barrier against the liquid while simultaneously allowing the article to breathe. Breathable films allow moisture vapor to pass through the film, which results in enhanced comfort to a wearer of an absorbent article since the release of moisture vapor reduces or eliminates a clammy sensation that often accompanies trapped moisture.

Breathable films can be produced by stretching a thermoplastic film containing a filler. Microvoids are created when the polymer separates from the filler particles during the stretching process. This drawing or stretching also orients the molecular structure within the film which increases the strength and durability of the film in the stretched direction. However, uni-directionally stretched films are easily torn or split along the cross-direction or transverse stretched direction. For example, a machine-directionally oriented film has a propensity to split or tear along the machine direction. Also, the tensile characteristics of the film are dramatically increased in the machine direction, but the tensile strength and tear-resistance in the cross-direction is significantly inferior to that of the machine direction.

One solution for remedying the durability problems of stretched filled films is to laminate the film to another layer of film, suitably one that does not have the same durability problems. However, any other layers in the laminate must also be breathable in order to maintain breathability throughout the laminate.

Lamination of films can also be used to combine materials that have a variety of material attributes. For example, laminating an elastomeric film to a stretched filled film may result in an elastomeric laminate. Elastomeric laminates provide better fit and conformance on a wearer, thus providing better leakage protection compared to non-elastomeric laminates and films. However, typical elastomeric films may reduce the breathability of the laminate. Additionally, elastomeric films are generally relatively expensive compared to stretched filled films. Furthermore, a number of elastomeric films are incompatible, or have low compatibility, with stretched filled films, resulting in a corrugated structure, or possibly delamination of the laminate. Controlled delamination of the laminate may provide certain benefits, such as loftiness and enhanced breathability, but uncontrolled delamination may result in a flimsy structure that detrimentally separates during use.

There is thus a need or desire for a breathable elastic laminate that is durable, and wherein the layers of the laminate are compatible with one another such that the layers are not prone to uncontrollable delamination.

SUMMARY OF THE INVENTION

In response to the discussed difficulties and problems encountered in the prior art, a new breathable elastic multilayer film laminate and method of making breathable elastic multilayer film laminates has been discovered. The laminate is particularly suitable for use in absorbent article applications such as waist and leg elastics, extensible and/or elastic outer covers, gasketing, and other closure applications, as well as in other disposable items.

The breathable elastic multilayer film laminate of the invention includes one or more layers of an inherently breathable elastic polymer and one or more layers of a plastic polymer filled with a filler so that when stretched the filled polymer produces a permanent microporous structure that is capable of moisture-vapor transmission. Hence the stretched composite structure produced is also breathable. Suitably, the laminate includes multiple layers of both the elastic polymer and the plastic polymer, with alternating layers of the elastic polymer and the plastic polymer. The laminate may include between about 10 wt % and about 90 wt % elastic polymer, and between about 10 wt % and about 90 wt % plastic polymer.

The elastic polymer includes a thermoplastic polymer grafted to an elastomer. By grafting a thermoplastic polymer to the elastic polymer, the elastic polymer may be modified to make it compatible, to a limited extent, with the more rigid plastic polymer. The thermoplastic polymer grafted elastomer suitably includes a polyolefin, such as polypropylene or polyethylene, grafted to a thermoplastic polyurethane. It is also possible to fill the inherently breathable elastomer with suitable filler, which upon stretching could also produce enhanced breathability. The presence of grafted polyethylene or polypropylene in one embodiment, for example, allows the formation of microvoids in a filled elastomer layer to provide a substantially breathable layer.

The filled plastic polymer may be linear low density polyethylene filled with between about 30 wt % and about 70 wt % calcium carbonate filler, for example. Adherence to elastic layers improves the tear resistance of the plastic polymer layers.

The laminate may further include a tie layer between a layer of the elastic polymer and a more rigid layer of the plastic polymer to adjust interlayer adhesion. In addition, facing layers may be bonded to outer layers of the laminate to produce a cloth-like surface that is aesthetically appealing.

The laminate of the invention is breathable, having a water vapor transmission rate (WVTR) of between about 1,000 and about 20,000 grams/$m^2$-24 hours. Overall thickness of the laminate is suitably between about 12 microns and about 120 microns. The laminate may be bonded reasonably well at its interfaces such that no corrugations are formed and no signs of delamination are evident. Alternatively, controlled delamination may be present and may be a desirable attribute from aesthetic (lofty) and functionality (enhanced breathability) points of view. Lofty structure caused by partial delamination may create a "spacer layer effect" that reduces the perception of dampness on the outside of the laminate when used as a diaper outer cover. Noise reduction may also be achieved through the dissipation of sound due to the lofty structure of the stretched and relaxed composite structure. In one embodiment, the laminate may be adjustably corrugated.

The laminate of the invention may be made by grafting a thermoplastic polymer to an elastomer to form an inherently breathable elastic polymer. The elastic polymer and the plastic polymer may be extruded through separate dies or through a multiblock die. While the polymers are in a melt-extrudable state, the extruded elastic polymer and the extruded plastic polymer are stacked, suitably alternating layers of the polymers, to create a multilayer film laminate. The laminate is stretched by about 100% to about 600%, either monoaxially or biaxially, to enhance breathability of the filled polymer(s). Once the laminate is stretched, the plastic layer should be gathered with the elastic layer creating an elastic laminate with a corrugated structure. The resulting laminate may either be monoaxially or biaxially stretchable. In one embodiment, the plastic polymer is used to form outer layers of the laminate for enhanced bonding of facing layers to the outer layers. Facing layers may be bonded to the laminate thermally, adhesively, or in any other suitable manner. The laminate may be heat-activated to elasticize any latent elastic polymers or laminate structures.

By grafting low-cost polyolefins to an otherwise more expensive elastomer, and combining layers including the more expensive elastomer with layers of low-cost filled polyolefin, a functional cost-efficient system may be produced.

With the foregoing in mind, it is a feature and advantage of the invention to provide a breathable elastic laminate having layers that are compatible with one another such that the laminate is durable, functional, and cost-efficient, and a method of making such laminates.

DEFINITIONS

Figure 1:
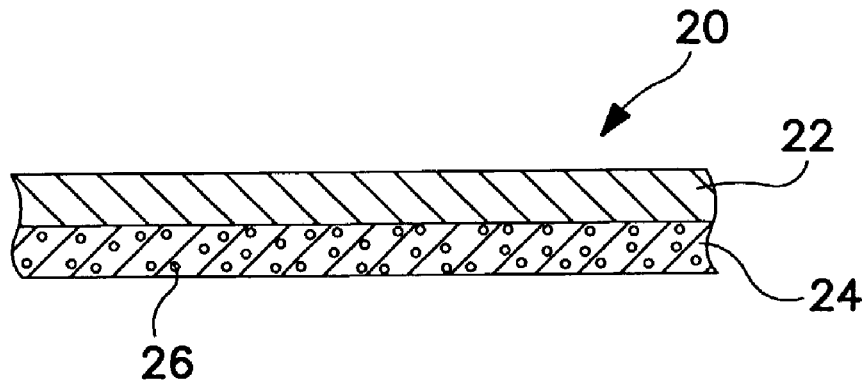
FIG. 1 is a schematic diagram of a two-layer laminate of the invention.

Within the context of this specification, each term or phrase below will include the following meaning or meanings.

"Absorbent article" includes personal care garments, medical garments, and the like. The term "disposable garment" includes garments which are typically disposed of after 1-5 uses. The term "personal care garment" includes diapers, diaper pants, training pants, swim wear, absorbent underpants, adult incontinence products, feminine hygiene products, personal health car gowns, and the like.

"Elastic" and "elastomeric" refer to a material or composite which can be elongated by at least 25 percent of its relaxed length and which will recover, upon release of the applied force, at least 10 percent of its elongation. It is generally desirable that the elastomeric material or composite be capable of being elongated by at least 100 percent, more desirably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Layer" when used in the singular can have the dual meaning of a single element or a plurality of elements.

"Linear low density polyethylene" refers to polymers of ethylene and higher alpha olefin comonomers, such as $C_2$-$C_{12}$ comonomers, and combinations thereof, having a density of about 0.900 to 0.935 grams/cm$^3$.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact.

"Low density polyethylene" refers to a polyethylene having a density between about 0.91 and about 0.925 g/cm$^3$.

"Machine direction" refers to the length of a fabric in the direction in which the fabric is produced, as opposed to "cross direction" which refers to a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Nonwoven" and "nonwoven web" refer to materials and webs of material which are formed without the aid of a textile weaving or knitting process.

"Plastic" refers to any of various organic compounds produced by polymerization, capable of being molded, extruded, cast into various shapes and films, or drawn into filaments used as textile fibers.

"Polymers" include, but are not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced, as known in the art. Spunbond fibers are quenched and generally not tacky when they are deposited onto a collecting surface. Spunbond fibers are generally continuous and often have average deniers larger than about 0.3, more particularly, between about 0.6 and 10.

"Thermoplastic" describes a material that softens when exposed to heat and which substantially returns to a nonsoftened condition when cooled to room temperature.

"Ultra low density polyethylene" refers to polymers of ethylene and higher alpha-olefin comonomers such as $C_3$-$C_{12}$ comonomers, and combinations thereof, having a density of about 0.860 to less than 0.900 g/cm$^3$.

These terms may be defined with additional language in the remaining portions of the specification.

DETAILED DESCRIPTION OF THE PRESENTLY PREFERRED EMBODIMENTS

The present invention is directed to breathable elastic film laminates including layers of an elastic polymer and layers of a filled plastic polymer, and methods of making such laminates.

Figure 2:
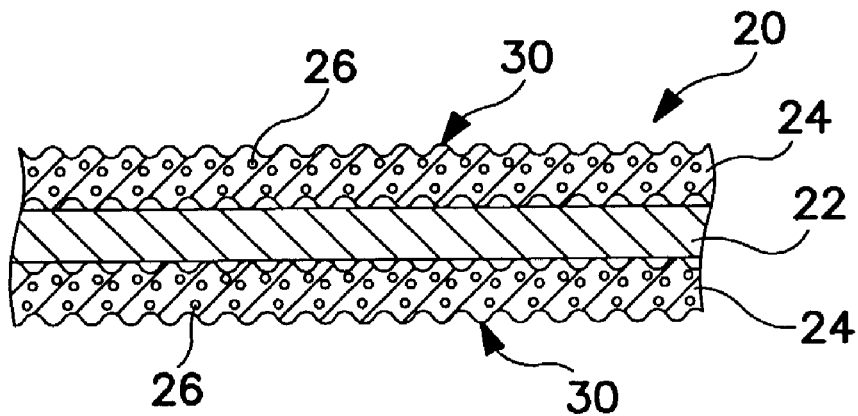
FIG. 2 is a schematic diagram of a three-layer laminate of the invention.
Figure 3:
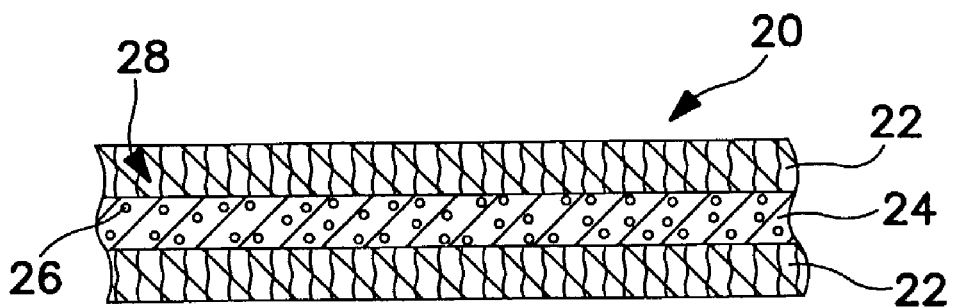
FIG. 3 is a schematic diagram of another three-layer laminate of the invention.
Figure 4:
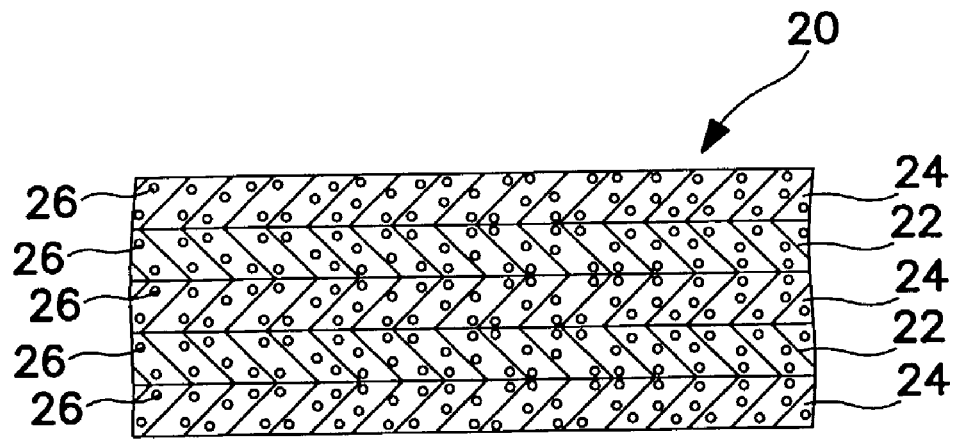
FIG. 4 is a schematic diagram of a five-layer laminate of the invention.
Figure 5:
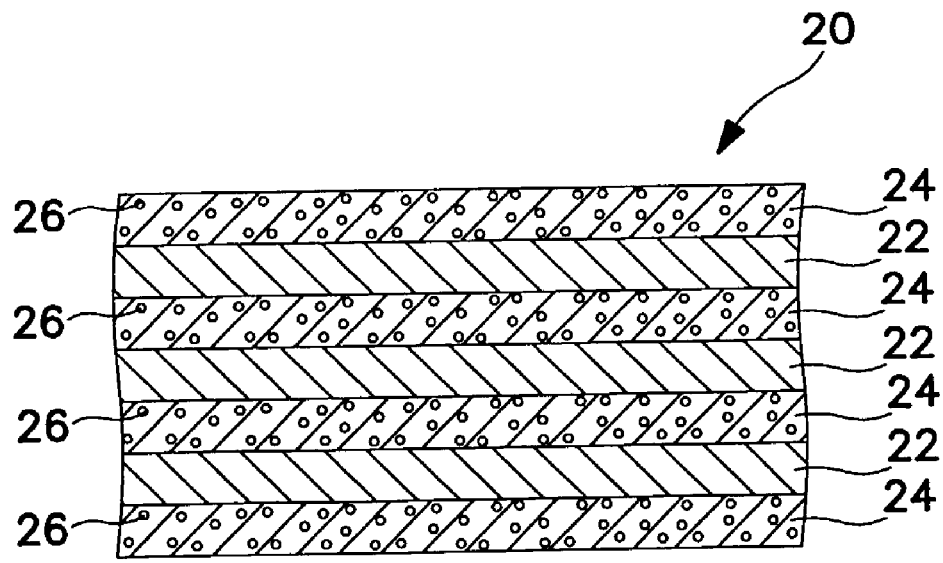
FIG. 5 is a schematic diagram of a seven-layer laminate of the invention.

A laminate 20 of the invention is shown in FIG. 1. The laminate 20 includes multiple layers of non-degradable polymers, including one or more layers of an inherently breathable elastic polymer film 22 and one or more layers of a filled plastic polymer 24. As shown in FIGS. 2 and 3, when multiple layers of the elastic polymer 22 and the plastic polymer 24 are present in the laminate 20, the layers are stacked in an alternating fashion. For example, as shown in FIG. 2, a layer of the elastic polymer 22 may be stacked between two layers of the plastic polymer 24, or, as shown in FIG. 3, a layer of the plastic polymer 24 may be stacked between two layers of the elastic polymer 22. Further examples of the laminate 20 of the invention are shown in FIG. 4, wherein the laminate 20 includes two layers of the elastic polymer 22 alternating with three layers of the plastic polymer 24, and in FIG. 5, wherein the laminate 20 includes three layers of the elastic polymer 22 alternating with four layers of the plastic polymer 24. The laminate 20 suitably includes between about 10% and about 90% elastic polymer, or between about 20% and about 80% elastic polymer, or between about 30% and about 70% elastic polymer. The laminate suitably includes between about 10% and about 90% filled or unfilled polymer, or between about 20% and about 80% filled or unfilled polymer, or between about 30% and about 70% filled or unfilled polymer.

The inherently breathable elastic polymer 22 includes a thermoplastic polymer grafted elastomer. For example, the thermoplastic polymer grafted elastomer may include a polyolefin grafted to a thermoplastic polyurethane (TPU). The polyolefin may be polypropylene, polyethylene, or any other suitable polyolefin. The compatibility of TPU to polyolefin-based elastomers or nonwoven materials can be improved if the TPU is grafted with small amounts of an olefin of interest. Although a dry blend of the olefin with TPU might provide sufficient compatibility, it is highly desirable to graft the olefinic polymer to the TPU. This can be accomplished by blending maleic anhydride grafted olefins to the TPU, mediated with or without a mono-, di-, or tri amine. The most preferred amine would be desired amounts of a di-amine, which couples the maleic anhydride to the TPU. The blending step could be done in-situ, in an extruder, or in a separate step in a reactor. The olefinic polymer could be plastic or a plastomer or an elastomer. The soft segment of the TPU can be ester, ether, or copolyetherester-based and the hard segment, a rigid moiety that tends to phase segregate form the soft segment. Some examples of hard segments are urea, urethane, amid, ether, or ester-based. In place of TPU, thermoplastic ether/ester elastomer can also be used. Polyolefins containing different levels of maleic anhydride grafting as well as a range of overall molecular weight, from low to high, can be used, depending on the desired ultimate performance of the blend/alloy. The thermoplastic polymer grafted elastomer may include between about 1% and about 70% polyolefin, or between about 5% and about 50% polyolefin, or between about 5% and about 20% polyolefin. Whatever is added to the elastomer, the entire elastic polymer 22 should remain elastic.

More specifically, suitable elastomeric polymers that may be used to make the inherently breathable elastic polymer include, without limitation, elastomeric (single-site or metallocene catalyzed) polypropylene, polyethylene and other alpha-olefin homopolymers and copolymers, having density less than about 0.89 grams/cc.

The single-site process for making polyolefins uses a single-site catalyst which is activated (i.e., ionized) by a co-catalyst. Polymers produced using single-site catalysts have a narrow molecular weight distribution. "Narrow molecular weight distribution polymer" refers to a polymer that exhibits a molecular weight distribution of less than about 3.5. As is known in the art, the molecular weight distribution of a polymer is the ratio of the weight average molecular weight of the polymer to the number average molecular weight of the polymer. Methods of determining molecular weight distribution are described in the *Encyclopedia of Polymer Science and Engineering*, Volume 3, Pages 299-300 (1985). Polydispersities ($M_w$/$M_n$) of below 3.5 and even below 2 are possible for single-site produced polymers. These polymers also have a narrow short chain branching distribution when compared to otherwise similar Ziegler-Natta produced polymers.

It is also possible to use a single-site catalyst system to control the isotacticity of the polymer quite closely when stereo selective metallocene catalysts are employed. In fact, polymers have been produced having an isotacticity in excess of 99 percent. It is also possible to produce highly syndiotactic polypropylene using this system.

Commercial production of single-site catalyzed polymers is somewhat limited but growing. Such polymers are available from ExxonMobil Chemical Company of Houston, Tex. under the trade name EXXPOL for polypropylene based polymers and EXACT for polyethylene based polymers. Dow Chemical Company of Midland, Mich. has polymers commercially available under the name AFFINITY. ENGAGE is another suitable polymer available from DuPont-Dow. These materials are believed to be produced using non-stereo selective single-site catalysts. ExxonMobil generally refers to their single-site catalyst technology as metallocene catalysts, while Dow refers to theirs as "constrained geometry" catalysts under the name INSITE to distinguish them from traditional Ziegler-Natta catalysts which have multiple reaction sites. Other manufacturers such as Fina Oil, BASF, BP, and Hoechst are active in this area and it is believed that the availability of polymers produced according to this technology will grow substantially in the next decade.

Regarding single-site catalyzed elastomeric polymers, U.S. Pat. No. 5,204,429 to Kaminsky et al. describes a process which may produce elastic copolymers from cycloolefins and linear olefins using a catalyst which is a stereorigid chiral metallocene transition metal compound and an aluminoxane. The polymerization is carried out in an inert solvent such as an aliphatic or cycloaliphatic hydrocarbon such as toluene. The reaction may also occur in the gas phase using the monomers to be polymerized as the solvent. U.S. Pat. Nos. 5,278, 272 and 5,272,236, both to Lai et al., assigned to Dow Chemical and entitled "Elastic Substantially Linear Olefin Polymers" describe polymers having particular elastic properties.

The filled plastic polymer 24 may be linear low density polyethylene, or other suitable plastic polymer, filled with a non-thermoplastic filler 26, such as calcium carbonate or other suitable filler. Other suitable plastic polymers 24 include low density polyethylene, ultra low density polyethylene, polypropylene-based elastomers, and metallocene-catalyzed elastomeric polymers such as those available from Dow Chemical Company of Midland, Mich., under the trade name AFFINITY, as mentioned above. The filler particles 26 suitably have a mean particle size of 5 microns or smaller, or 2 microns or smaller. The filler particles 26 in the plastic polymer 24 initiate the formation of voids surrounding the particles upon stretching the plastic polymer film 24. The voids impart breathability to the plastic polymer layer(s) by creating a tortuous path of thin membranes through which water vapor, but not liquid water, can pass. Examples of microporous films are described in U.S. Pat. No. 5,695,868 issued to McCormack, U.S. Pat. No. 5,932,497 issued to Morman, et al., U.S. Pat. No. 6,045,900 issued to Haffner, et al., and U.S. Pat. No. 6,072,005 issued to Kobylivker, et al., all of which are hereby incorporated by reference. The filler may account for between about 30% and about 70%, or between about 40% and about 60% of the filled plastic polymer by weight of the filled plastic polymer.

In one embodiment of the invention, represented in FIG. 4, the inherently breathable elastic polymer 22 may also be filled with a filler 26 in the same manner described above with respect to the plastic polymer 24. The presence of grafted polyethylene or polypropylene in the elastomer 22 may enhance the ability of the filled elastomer to provide a substantially breathable layer.

By grafting a thermoplastic polymer to the elastic polymer 22, the elastic polymer may be modified to make it compatible, to a limited extent, with the more rigid plastic polymer 24. The layers of the laminate 20 can be bonded to one another using any suitable bonding technique, such as thermal bonding, adhesive bonding, ultrasonic bonding, and the like. Because of the compatibility between the thermoplastic polymer grafted elastomer 22 and the plastic polymer 24, the layers may be bonded so well at their interfaces such that no signs of delamination are observed during or after use. Another result of the relatively strong bonding between the grafted elastomer 22 and the plastic polymer 24 is that corrugations are not necessarily formed in the laminate upon stretching and relaxing. In fact, the interface bonding can be so strong such that when the filled system cavitates or crazes under stretching the micropores or microcracks 28 could propogate from the filled layer 24 to the non-filled layer 22 thus providing a path for breathability. Furthermore, cavitation and crazing lead to opaqueness, and as a result, use of these laminates 20 as outer cover materials provides a product through which stains due to soiling do not appear.

Other benefits of using a thermoplastic polymer grafted elastomer 22 in the laminate 20 include improving the tear resistance of the film. Furthermore, by grafting low-cost polyolefins to an otherwise more expensive elastomer, a low-cost system may be produced. Additionally, by combining layers of the more expensive thermoplastic elastomer 22 with layers of low-cost filled polyolefin 24, a functional, cost-efficient system is further produced.

In another embodiment of the invention, controlled delamination at the interfaces may be desirable. If the interface of the layers is relatively weak, partial delamination may occur, thus providing a structure that is lofty and having enhanced breathability attributable to the development of additional paths providing transportation of water vapor. The lofty structure caused by partial delamination may create a "spacer layer effect" that reduces the perception of dampness on the outside of the laminate when used as an outer cover of an absorbent garment. Furthermore, the lofty structure may provide noise reduction through the dissipation of sound due to the loftiness of the stretched and relaxed composite structure.

Partial delamination, or controlled delamination, may be achieved by adjustably controlling the formation of corrugations 30 in the laminate 20, as shown in FIG. 2. Adjustable corrugations 30 can be achieved by determining the mechanical buckling instability of the plastic polymer 24 under compressive force and stretching the laminate 20 accordingly, as explained in detail in the article "Mechanical Buckling Instability of Thin Coatings Deposited on Soft Polymer Substrates," by A. L. Volynskii et al. in the Journal of Materials Science 35 (2000) 547-554, hereby incorporated by reference.

Figure 6:
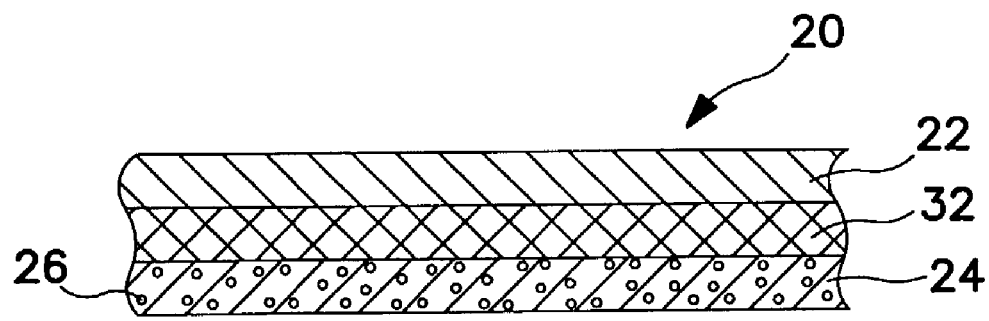
FIG. 6 is a schematic diagram of a laminate of the invention including a tie layer.

As illustrated in FIG. 6, the laminate 20 of the invention may further include an additional layer, namely a tie layer 32, between elastic polymer layers 22 and the more rigid plastic polymer layers 24 to adjust interlayer adhesion. The tie layer 32 can be formed from a variety of melt-extrudable polymers. Suitable polymers for the tie layer 32 depend on the particular polymers used for the elastic polymer layers 22 and the plastic polymer layers 24, but generally include block copolymers of polyesters and polyethers, polyolefin block copolymers, filled polyesters, filled polyolefins, and blends and mixtures thereof. For example, ethylene vinyl acetate polymers can be used as a tie layer.

Figure 7:
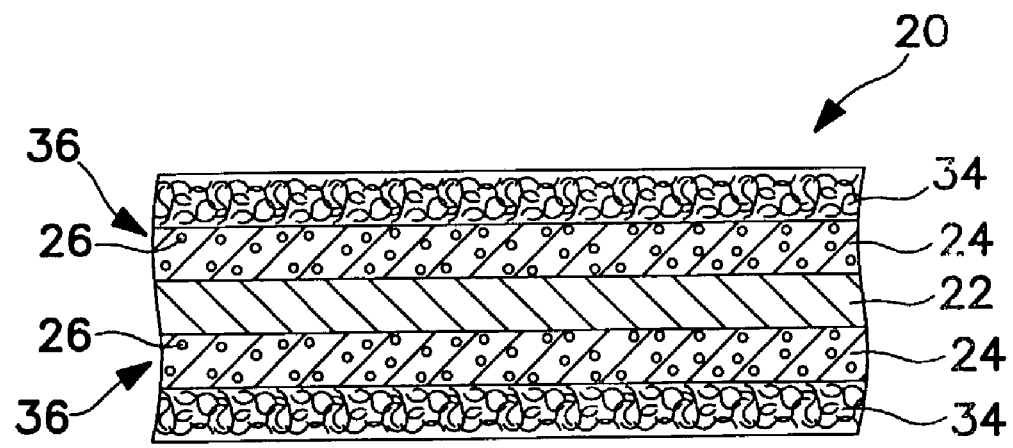
FIG. 7 is a schematic diagram of a laminate of the invention including two facing layers bonded to outer layers of the laminate.

To form a cloth-like, aesthetically pleasing surface on the laminate 20, facing layers 34 may be bonded to one or more of the outer layers 36 of the laminate 20, as shown in FIG. 7. Facing materials 34 may be nonwoven webs formed using conventional processes, including the spunbond and meltblowing processes described in the DEFINITIONS, to achieve, for example, spunbond webs, bicomponent spunbond webs, bonded carded webs, meltblown webs, hydroentangled webs, spunbond-meltblown-spunbond laminates, or necked or inherently extensible/elastic webs. For example, the facing layers 34 may each include a spunbond web having a basis weight of about 0.1-4.0 ounces per square yard (osy), suitably 0.2-2.0 osy, or about 0.4-0.6 osy. The facing layers 34 in a single laminate 20 may include the same or similar materials or different materials. The choice of outer layer polymers 36 may be based on the ease with which the polymers can be thermally bonded to the facing layers 34. For example, if an outer layer 36 of the laminate 20 is filled polypropylene, the outer layer 36 can be easily bonded to a polypropylene-based spunbond facing 34.

The breathability of the laminate 20 is expressed as water vapor transmission rate (WVTR). The WVTR is a function of both laminate thickness and polymer composition. The laminate suitably can deliver moderate breathability in a range of about 1,000 to 20,000, or about 3,000 to 15,000 grams/m$^2$-24 hours using the Mocon WVTR test procedure described below.

Overall thickness of the laminate 20 depends on the number of layers, and is generally in a range of between about 12 and about 120 microns, or between about 20 and about 50 microns.

Figure 8:
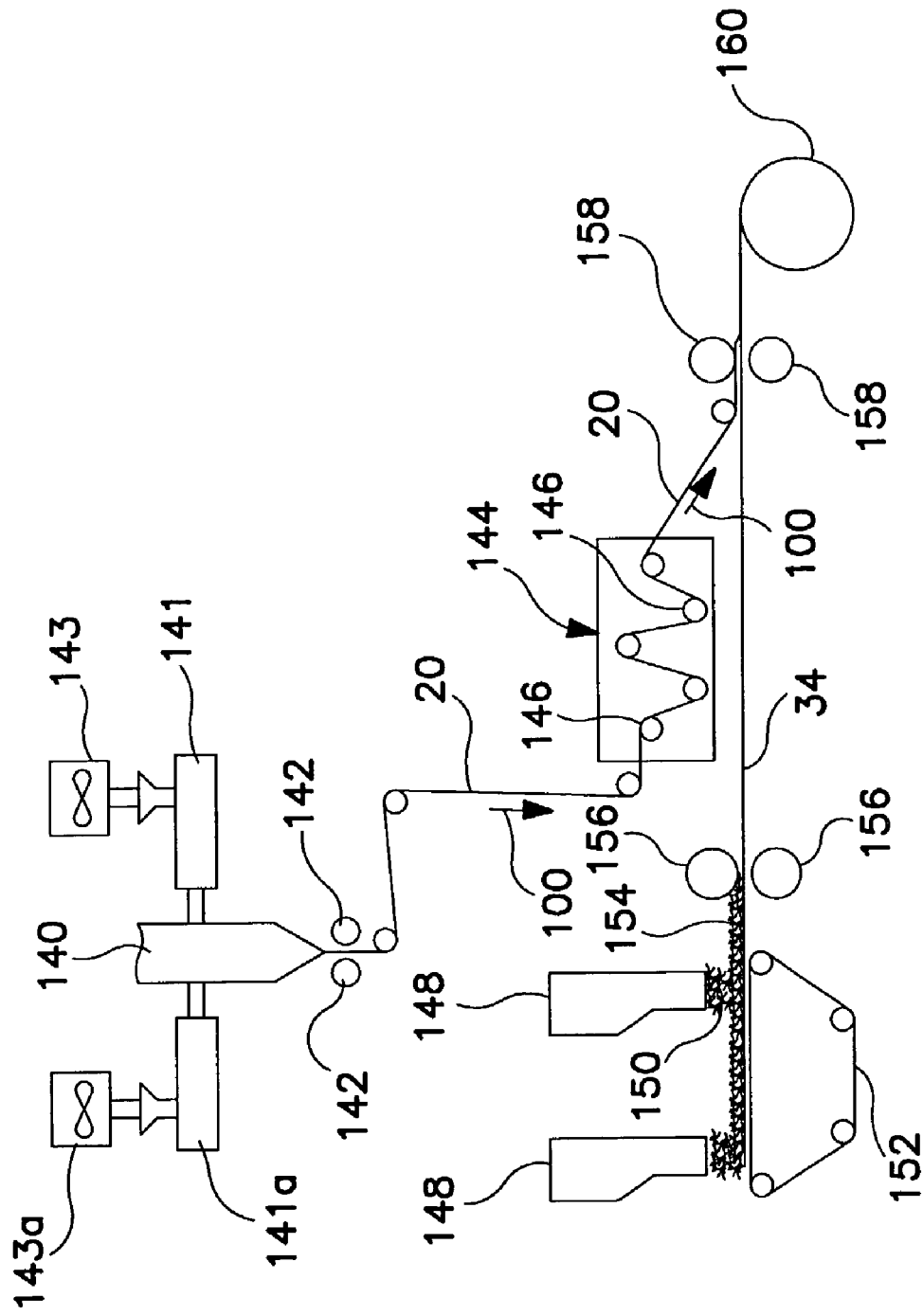
FIG. 8 is a schematic diagram of a process for preparing a laminate of the invention.

An illustration of a process for making the breathable elastic film laminate 20 is shown in FIG. 8. As shown in FIG. 8, the laminate 20 is formed from a film extrusion apparatus 140 such as a cast or blown unit. The apparatus 140 may include two or more extruders 141, 141a and two or more dies, with the elastomer 22 and the plastic polymer 24 passing through separate extruders and dies, or alternatively, the apparatus 140 may include two extruders with a multiblock die through which both the elastomer and the plastic polymer pass (not shown). Multilayer coextrusion devices and processes useful for this invention are described in an article by W. J. Schrenk and T. Alfrey, Jr., entitled "Coextruded Multilayer Polymer Films and Sheets," Polymer Blends, vol. 2, p. 129, Academic Press, Inc. (1978), herein incorporated by reference.

The plastic polymer 24 and filler 26 are mixed in a mixer 143 and directed to the extruder 141. The thermoplastic polymer grafted elastomer 22 is prepared in another mixer 143a and is also directed to an extruder 141a. The laminate 20 is coextruded through one or more dies such that the elastomer and plastic polymer layers are stacked, suitably alternating layers of the elastomer with layers of the plastic polymer, while in a melt-extrudable state to create the multilayer film laminate. A tie layer 32 may be extruded between elastomer and plastic polymer layers simultaneously during the extrusion process. The laminate 20 is directed into a pair of nip or chill rollers 142, one of which may be patterned so as to impart an embossed pattern to the newly formed laminate.

From the film extrusion apparatus 140, the laminate 20 is directed to a film stretching unit 144 such as a machine direction orienter, which is a commercially available device from vendors such as the Marshall and Williams Company of Providence, R.I. Such an apparatus 144 has a plurality of stretching rollers 146 moving at progressively faster speeds relative to the pair disposed before it. These rollers 146 apply an amount of stress and thereby progressively stretch the laminate 20 to a stretch length in the machine direction of the film (indicated by arrow 100 in FIG. 8) which is the direction of travel of the laminate 20 through the process as shown in FIG. 8. The stretch rollers 146 may be heated for better processing. Suitably, the stretching unit 144 also includes rollers (not shown) upstream and/or downstream from the stretch rollers 146 that can be used to preheat the laminate 20 before orienting and/or anneal (or cool) it after stretching.

Alternatively, instead of or in addition to stretching the laminate 20 in the machine direction, the laminate may be stretched in the cross direction. In other words, the laminate may be either monoaxially or biaxially stretched, with the monoaxial stretching occurring in either the machine direction or the cross direction. Thus, the resulting laminate may be monoaxially stretchable in either the machine direction or the cross direction, or may be biaxially stretchable in both the machine direction and the cross direction. Suitably, the laminate is stretched between about 100% and about 600%, or between about 150% and about 500%. Stretching creates micropores in the filled film(s) of the laminate.

As shown in FIG. 8, the laminate 20 can be bonded to one or more facing layers 34 to enhance strength and durability of the laminate, as well as to provide an aesthetically pleasing cloth-like texture to a surface of the laminate. The facing layer(s) 34, suitably nonwoven webs as described above, may be either pre-formed or may be produced within the same process as the laminate formation process. In the latter embodiment, a conventional fibrous nonwoven web forming apparatus 148, such as a pair of spunbond banks, can be used to form the facing layer 34. Long, essentially continuous fibers 150 are deposited onto a forming wire 152 as an unbonded web 154 and the unbonded web 154 is then sent through a pair of bonding rolls 156 to bond the fibers together and increase the tear strength of the resultant facing layer 34. One or both of the rolls 156 are often heated to aid in bonding. Typically, one of the rolls 156 is also patterned so as to impart a discrete bond pattern with a prescribed bond surface area to the web. The other roll 156 is usually a smooth anvil roll but this roll also may be patterned if so desired. Once the film laminate 20 has been sufficiently stretched and the facing layer 34 has been formed, the laminate 20 and the facing layer 34 are brought together and bonded to one another using a pair of laminating rolls 158 or other means. As with the bonding rolls 156, the laminating rolls 158 may be heated. Also, at least one of the rolls may be patterned to create a discrete bond pattern with a prescribed bond surface area for the resultant laminate. Once the laminate exits the laminating rolls 158, it may be wound up into a roll 160 for subsequent processing. Alternatively, the laminate may continue in-line for further processing or conversion.

In one embodiment, it may be particularly desirable for the laminate 20 to include the plastic polymer 24 as at least one of the outer layers 36 of the laminate for ease in thermally bonding the nonwoven facing layer 34 to the laminate 20. For example, if the outer layer of the multilayer structure is filled propylene, it can be easily bonded to a polypropylene-based spunbond facing layer.

While the facing layer 34 and film laminate 20 shown in FIG. 8 were bonded together through thermal bonding, other types of bonding can also be used. Suitable alternatives include, for example, adhesive bonding. In adhesive bonding, an adhesive such as a hot melt adhesive is applied between the laminate and the nonwoven fiber material to bind the film and the nonwoven together. The adhesive can be applied by, for example, melt spraying, printing or meltblowing. Various types of adhesives are available including those produced from amorphous polyalphaolefins and ethylene vinyl acetate-based hot melts.

The laminate 20 may also include one or more latent elastic materials, such as polyester segmented-block polyurethane, polyether segmented-block polyurethane, and/or polyether block polyamide copolymers. As an example, polyether block polyamide PEBAX 2533 elastomer, available from Ato Chemical Company, in Philadelphia, Pa., can be used as a latent elastic. After the laminate has been formed, the laminate may be heated to heat-activate any latent elastic materials. Although the amount of heat depends on the specific heat-activatable materials, the laminate can generally be heated between about 50 and about 100 degrees Celsius.

The laminates 20 of the invention can be incorporated into any suitable end-product. The laminates are particularly suitable for use in absorbent articles. Examples of suitable absorbent articles include personal care garments, medical garments, and other disposable garments. The elastic properties of the laminate render the laminate suitable for such applications as waist and leg elastics, extensible and/or elastic outer covers, gasketing, and other closure applications, thereby providing improved fit and conformance of the product on a wearer compared to other types of elastic materials, thus providing improved leakage protection as well.

Figure 9:
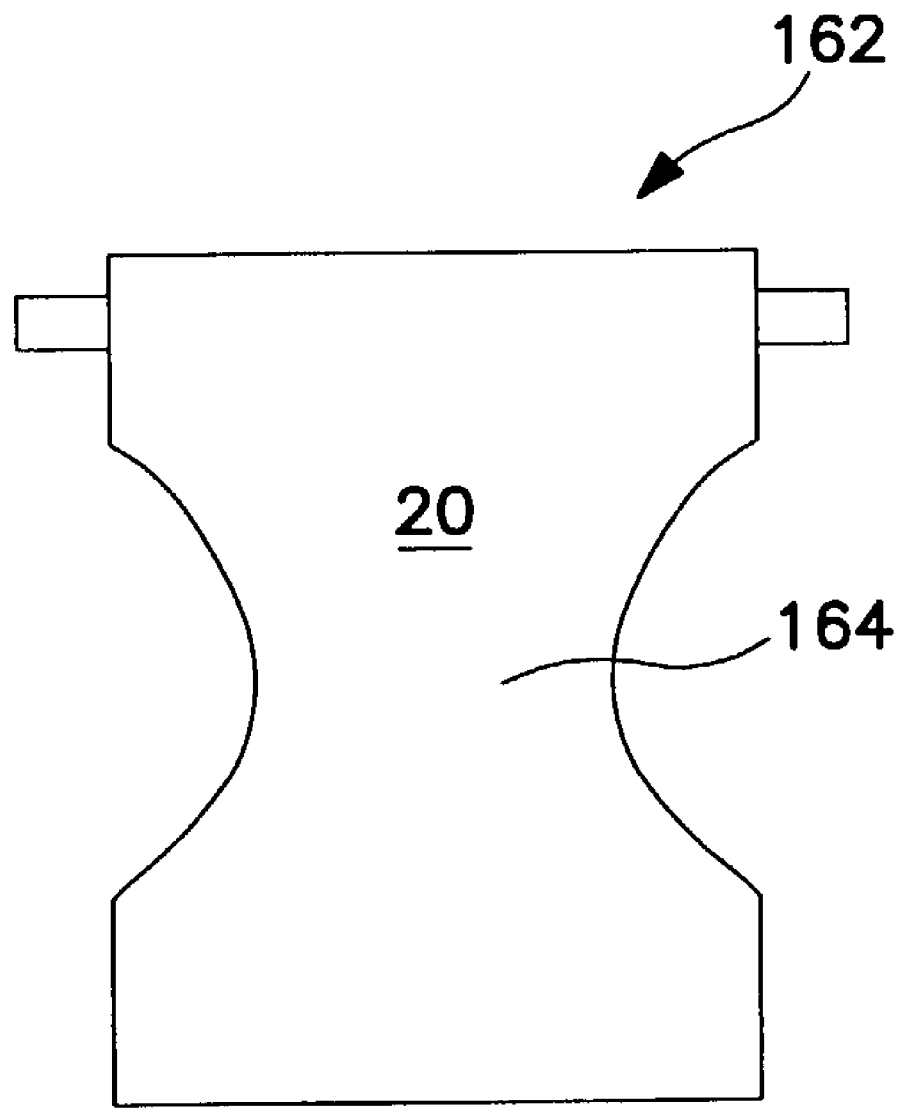
FIG. 9 is a schematic diagram of an absorbent article including a laminate of the invention.
Figure 10:
FIG. 10 is an SEM of a laminate of the invention, showing the corrugated structure.

An absorbent article 162, namely a diaper, having an outer cover 164 made up of the laminate 20 of the invention is shown in FIG. 9. The laminate 20 is particularly suitable for use as an outer cover 164 because the laminate provides breathability, elastic properties, as well as dampness mitigation capability without requiring a separate spacer layer. More specifically, when the multi-layer film is stretched or otherwise oriented in the machine direction (MD) and subsequently relaxed, the multi-layer film develops an internal corrugated structure, as shown in an SEM cross-sectional view in FIG. 10. The corrugated structure creates "air pockets" which may provide the same function as a separate spacer layer, thereby eliminating a need for a separate spacer layer.

Without wishing to be bound by theory, it is believed that the corrugated structure is a consequence of the elastic polyurethane layers' ability to retract in combination with the filled film layers' inability to retract. Essentially, the filled layers buckle when the polyurethane layers retract. The composition of the multi-layer film or film laminate can be tailored to meet the desired outer cover laminate properties by varying the polymers used in the layers, the layer ratio, the number of layers, the amount of filler, and/or the type of filler. With nonwoven facings 34 (FIG. 7) on the multi-layer film, the resulting laminate further provides cloth-like aesthetics which are desirable for the outer covers of absorbent articles.

EXAMPLES

Example 1

In this example, a thermoplastic polyurethane elastomer polymer containing 10% polypropylene (polypropylene-g-thermoplastic polyurethane) that was partially grafted was extruded and fed into three channels of a die while a 56% calcium carbonate ($CaCO_3$) filled linear low density polyethylene (UB-12) was extruded from a second extruder and was fed into four other channels of the feed block of the same die. The layers were arranged such that the elastic and plastic layers alternate to form a seven-layered composite structure capable of stretching and retracting. The outer layers included films of the filled completely non-tacky polyethylene polymer. The structure was monoaxially and biaxially stretched several times its original dimension. The multilayer structure was thermally bonded reasonably well at the interfaces such that no signs of delamination were observed.

Example 2

In this example, a seven-layer film laminate was formed of the same type of polypropylene-g-thermoplastic polyurethane (TPU) and the same type of UB-12 filled linear low density polyethylene (PE) used in Example 1, above, in alternating sequence (PE/TPU/PE/TPU/PE/TPU/PE). In this laminate, the amount of calcium carbonate filler in the polyethylene layers varied, with the polyethylene layers having the following ratios of calcium carbonate to linear low density polyethylene: 50/50, 60/40, 70/30, and 90/10. The TPU elastomer layers were not filled. The resulting 1 mil thick multilayer laminate was bonded to a spunbond facing using transfer adhesive on one side of the laminate. The resulting latent structure was then heat-activated to obtain an elastic laminate.

Figure 11:
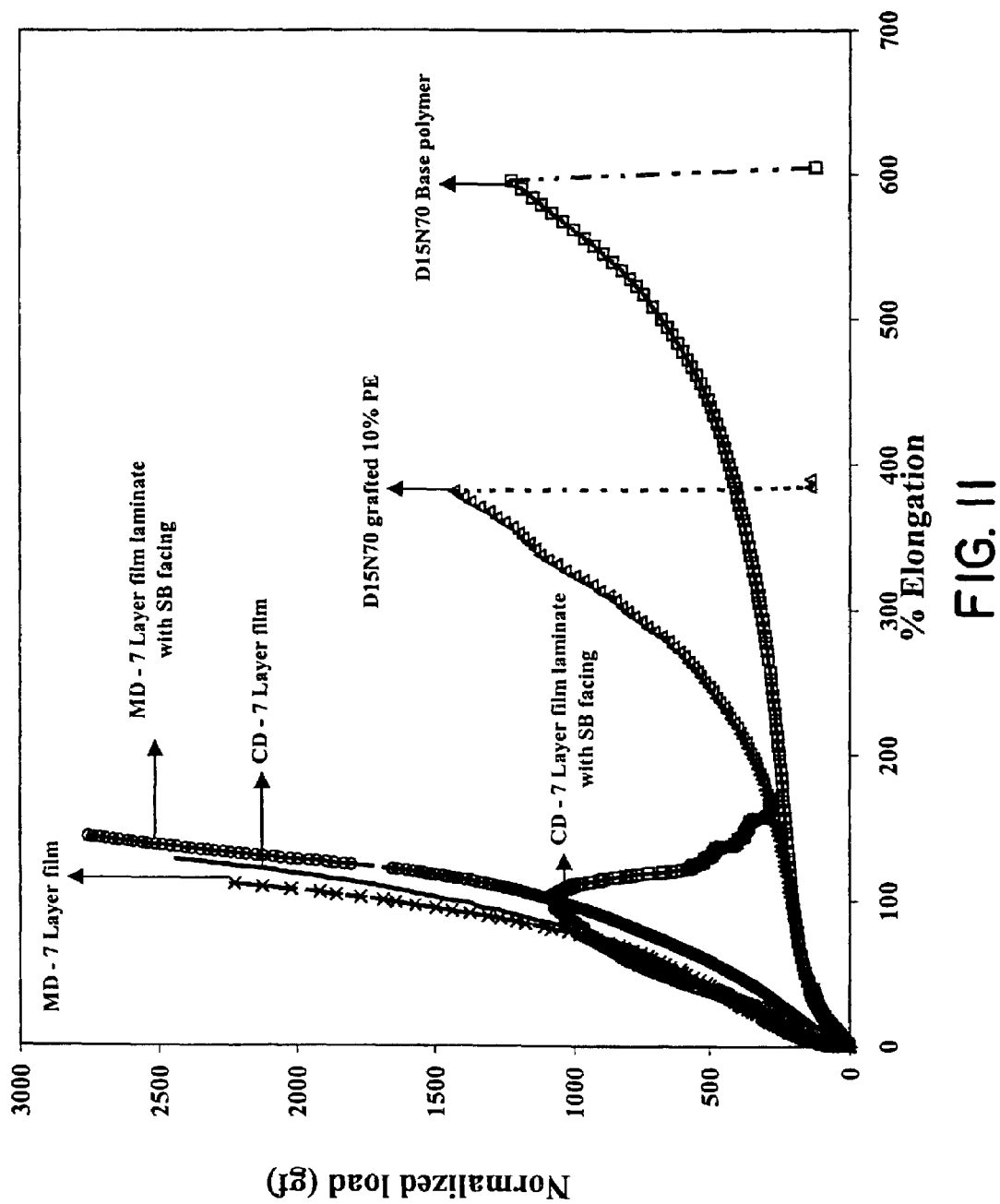
FIG. 11 is a graph showing load-elongation behavior of the laminate of the invention.

Load-elongation behavior of the seven-layer film laminate, the seven-layer film laminate with spunbond facing, the base polymer alone, and the grafted polymer alone were tested and compared. Results are shown in FIG. 11. The laminate structures were stretched biaxially. As can be seen in FIG. 11, the base thermoplastic polyurethane (D15N70, a TPU polymer based polyether/ester copolymer rubber available from Merquinsa in Spain) alone has a normalized load of about 1200 grams force (gf) at 600% elongation. When grafted to 10% maleic anhydride, the same TPU has a normalized load of about 1500 gf at just under 400% elongation. The films included 90% TPU elastomer and 10% of 58% calcium carbonate filled linear low density polyethylene. The load-elongation behavior of the seven-layer film laminate and the seven-layer film laminate with spunbond facing is shown for both cross-direction (CD) and machine-direction (MD) stretch in FIG. 11.

Example 3

In this example, 14 different laminates were formed using between two and four extruders. In addition to the different processing conditions used to create these laminates, the resulting laminates also varied in composition, number of layers, and overall thickness. The data from each of the laminate processes are provided below in Tables 1-14.

One of the compositions appearing in the tables (Tables 7-11) is UB12, which includes 58% calcium carbonate, 26.8% linear low density polyethylene from Dow Chemical Co., 15% EXACT plastomer polymer from ExxonMobil, and 0.2% antioxidant. Another composition, SAM06150 (in Tables 1-6), is similar to UB12 with the only difference being that the Dow linear low density polyethylene is a different grade. Both UB12 and SAM06150 contain 58% calcium carbonate filler. Other polymers, such as Noveon's ESTANE 58680 (Table 13), DuPont's SURLYN 1702 (Tables 12-14), and Atofina's PEBAX (Table 14), are familiar to those skilled in the art. Polyurethane film samples were not filled.

TABLE 1

Laminate #1

| | | | | | | | |
|---|---|---|---|---|---|---|---|
| | | Gauge | | 0.0018 | Air Gap | | Cost |
| | | Width | | 22" | Emboss Pattern | | 20RA |
| | | Footage | | 1500 | CO-EX Block | | BA |
| | | Treat | | NONE | AB 50/50, BAB 10/80/10 | | |
| | | | | | BAB 20/60/20 | | |
| SCREWS | STD | A | 20-100-20 | C NA | CBAD 10/40/40/10 | | |
| DIE | 33" | B | 20-150-20 | D NA | CADBDAC | | |
| | FG | | | | 10/20/10/20/20/20/10 | | |

| | Ratio | | | | | | |
|---|---|---|---|---|---|---|---|
| Primary Roll fpm | 68 | Tension Pot | 8% | Ext. B rpm | 15 | Ext. C rpm | NA |
| Anneal Roll fpm | 68 | Taper Pot | 30% | Ext. B amps | 14 | Ext. C amps | NA |
| | 1.0 | | | | | | |
| Cooling Roll fpm | — | Tension | 2.6% | Ext. A rpm | 35 | Ext. D rpm | NA |
| Winder Nip fpm | 68 | Vac Box rpm | 27% | Ext. A amps | 50 | Ext. D amps | NA |
| | 1.005 | | | | | | |

TABLE 1-continued

Laminate #1

| Extruder B | | Extruder A | | Extruder C | | Extruder D | |
|---|---|---|---|---|---|---|---|
| Extruder B | 30% | Extruder A | 70% | Extruder C | 0% | Extruder D | 0% |
| SCC SAM 06150 | 100 | LM 305-10 | 100 | | | | 100 |
| | | | | NA | | NA | |
| Total | 0 | | 0 | | 0 | | 0 |

| Extruder B | | Extruder A | | Extruder C | | Extruder D | |
|---|---|---|---|---|---|---|---|
| Barrel Zone 1 | 330 | Barrel Zone 1 | 340 | Barrel Zone 1 | NA | Barrel Zone 1 | NA |
| Barrel Zone 2 | 350 | Barrel Zone 2 | 370 | Barrel Zone 2 | | Barrel Zone 2 | |
| Barrel Zone 3 | 380 | Barrel Zone 3 | 380 | Barrel Zone 3 | | Barrel Zone 3 | |
| Barrel Zone 4 | 400 | Barrel Zone 4 | 400 | Screen Ch. 1 | | Screen Ch. 1 | |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | | Conn. Pipe 2 | |
| Screen Ch. 3 | | Screen Ch. 3 | | Conn. Pipe 3 | | Conn. Pipe 3 | |
| Valve Zone 1 | | Valve Zone 1 | | Pressure 1 | | Pressure 1 | |
| Conn. Pipe 1 | | Conn. Pipe 1 | | Pressure 2 | | Pressure 2 | |
| Conn. Pipe 2 | 400 | Conn. Pipe 2 | | Melt Temp 1 | | Melt Temp 1 | |
| Die Zone 1 | 420 | Conn. Pipe 3 | | Melt Temp 2 | | Melt Temp 2 | |
| Die Zone 2 | | CO-block 1 | 400 | | | | |
| Die Zone 3 | | CO-block 2 | | | | | |
| Die Zone 4 | | CO-block 3 | | | Treat | | Roll Temp |
| Die Zone 5 | 420 | CO-block 4 | 400 | Top/Bottom | | Chill Roll | 70 |
| Melt Temp 1 | 381 | Melt Temp 1 | 382 | Volts | | Anneal Roll | 70 |
| Melt Temp 2 | 414 | Melt Temp 2 | 383 | Amos | | Cooling Roll | |
| Pressure 1 | 1270 | Pressure 1 | 1700 | KW | | | |
| Pressure 2 | 840 | Pressure 2 | 780 | | | | |

TABLE 2

Laminate #2

| | | | | | | | |
|---|---|---|---|---|---|---|---|
| | Gauge | | 0.0018 | Air Gap | | Cost | |
| | Width | | 22" | Emboss Pattern | | 20RA | |
| | Footage | | 1500 | CO-EX Block | | BA | |
| | Treat | | NONE | AB 50/50, BAB 10/80/10 | | | |
| SCREWS | STD | A | 20-100-20 | C NA | BAB 20/60/20 CBAD 10/40/40/10 | | |
| DIE | 33" FG | B | 20-150-20 | D NA | CADBDAC 10/20/10/20/20/20/10 | | |

| | Ratio | | | | | | |
|---|---|---|---|---|---|---|---|
| Primary Roll fpm | 80 | Tension Pot | 8% | Ext. B rpm | 23 | Ext. C rpm | NA |
| Anneal Roll fpm | 81 | Taper Pot | 30% | Ext. B amps | 20 | Ext. C amps | NA |
| | 1.0 | | | | | | |
| Cooling Roll fpm | — | Tension | 2.6% | Ext. A rpm | 35 | Ext. D rpm | NA |
| Winder Nip fpm | 81 | Vac Box rpm | 27% | Ext. A amps | 50 | Ext. D amps | NA |
| | 1.005 | | | | | | |

| Extruder B | | Extruder A | | Extruder C | | Extruder D | |
|---|---|---|---|---|---|---|---|
| Extruder B | 40% | Extruder A | 60% | Extruder C | 0% | Extruder D | 0% |
| SCC SAM 06150 | 100 | LM 305-10 | 100 | | | | 100 |
| | | | | NA | | NA | |
| Total | 0 | | 0 | | 0 | | 0 |

| Extruder B | | Extruder A | | Extruder C | | Extruder D | |
|---|---|---|---|---|---|---|---|
| Barrel Zone 1 | 330 | Barrel Zone 1 | 340 | Barrel Zone 1 | NA | Barrel Zone 1 | NA |
| Barrel Zone 2 | 350 | Barrel Zone 2 | 370 | Barrel Zone 2 | | Barrel Zone 2 | |
| Barrel Zone 3 | 380 | Barrel Zone 3 | 380 | Barrel Zone 3 | | Barrel Zone 3 | |
| Barrel Zone 4 | 400 | Barrel Zone 4 | 400 | Screen Ch. 1 | | Screen Ch. 1 | |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | | Conn. Pipe 2 | |
| Screen Ch. 3 | | Screen Ch. 3 | | Conn. Pipe 3 | | Conn. Pipe 3 | |
| Valve Zone 1 | | Valve Zone 1 | | Pressure 1 | | Pressure 1 | |
| Conn. Pipe 1 | | Conn. Pipe 1 | | Pressure 2 | | Pressure 2 | |
| Conn. Pipe 2 | 400 | Conn. Pipe 2 | | Melt Temp 1 | | Melt Temp 1 | |
| Die Zone 1 | 420 | Conn. Pipe 3 | | Melt Temp 2 | | Melt Temp 2 | |

TABLE 2-continued

Laminate #2

| | | | | | | | |
|---|---|---|---|---|---|---|---|
| Die Zone 2 | | CO-block 1 | 400 | | | | |
| Die Zone 3 | | CO-block 2 | | | | | |
| Die Zone 4 | | CO-block 3 | | | Treat | | Roll Temp |
| Die Zone 5 | 420 | CO-block 4 | 400 | Top/Bottom | | Chill Roll | 70 |
| Melt Temp 1 | 387 | Melt Temp 1 | 383 | Volts | | Anneal Roll | 70 |
| Melt Temp 2 | 417 | Melt Temp 2 | 383 | Amos | | Cooling Roll | |
| Pressure 1 | 1580 | Pressure 1 | 1750 | KW | | | |
| Pressure 2 | 1060 | Pressure 2 | 840 | | | | |

TABLE 3

Laminate #3

| | | | | | | | | | |
|---|---|---|---|---|---|---|---|---|---|
| | | Gauge | | 0.0018 | Air Gap | | | Cost | |
| | | Width | | 22" | Emboss Pattern | | | 20RA | |
| | | Footage | | 600 | CO-EX Block | | | BA | |
| | | Treat | | NONE | AB 50/50, BAB 10/80/10 | | | | |
| | | | | | BAB 20/60/20 | | | | |
| SCREWS | STD | A | 20-100-20 | C NA | CBAD 10/40/40/10 | | | | |
| DIE | 33" | B | 20-150-20 | D NA | CADBDAC | | | | |
| | FG | | | | 10/20/10/20/20/20/10 | | | | |

| | | Ratio | | | | | | | |
|---|---|---|---|---|---|---|---|---|---|
| Primary Roll fpm | 60 | | Tension Pot | 10% | Ext. B rpm | 15 | Ext. C rpm | NA | |
| Anneal Roll fpm | 61 | 1.0 | Taper Pot | 30% | Ext. B amps | 14 | Ext. C amps | NA | |
| Cooling Roll fpm | 61 | 1.0 | Tension | 2.8% | Ext. A rpm | 35 | Ext. D rpm | NA | |
| Winder Nip fpm | 61 | 1.005 | Vac Box rpm | 27% | Ext. A amps | 42 | Ext. D amps | NA | |

| | | | | | | | |
|---|---|---|---|---|---|---|---|
| Extruder B | 30% | Extruder A | 70% | Extruder C | 0% | Extruder D | 0% |
| SCC SAM 06150 | 87 | LM 205-10 | 100 | | | | 100 |
| Dow 2035 | 13 | | | NA | | NA | |
| Total | 0 | | 0 | | 0 | | 0 |

| Extruder B | | Extruder A | | Extruder C | | Extruder D | |
|---|---|---|---|---|---|---|---|
| Barrel Zone 1 | 330 | Barrel Zone 1 | 340 | Barrel Zone 1 | NA | Barrel Zone 1 | NA |
| Barrel Zone 2 | 350 | Barrel Zone 2 | 370 | Barrel Zone 2 | | Barrel Zone 2 | |
| Barrel Zone 3 | 380 | Barrel Zone 3 | 380 | Barrel Zone 3 | | Barrel Zone 3 | |
| Barrel Zone 4 | 400 | Barrel Zone 4 | 400 | Screen Ch. 1 | | Screen Ch. 1 | |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | | Conn. Pipe 2 | |
| Screen Ch. 3 | | Screen Ch. 3 | | Conn. Pipe 3 | | Conn. Pipe 3 | |
| Valve Zone 1 | | Valve Zone 1 | | Pressure 1 | | Pressure 1 | |
| Conn. Pipe 1 | | Conn. Pipe 1 | | Pressure 2 | | Pressure 2 | |
| Conn. Pipe 2 | 400 | Conn. Pipe 2 | | Melt Temp 1 | | Melt Temp 1 | |
| Die Zone 1 | 420 | Conn. Pipe 3 | 380 | Melt Temp 2 | | Melt Temp 2 | |
| Die Zone 2 | | CO-block 1 | 400 | | | | |
| Die Zone 3 | | CO-block 2 | | | | | |
| Die Zone 4 | | CO-block 3 | | | Treat | | Roll Temp |
| Die Zone 5 | 420 | CO-block 4 | 400 | Top/Bottom | | Chill Roll | 70 |
| Melt Temp 1 | 374 | Melt Temp 1 | 377 | Volts | | Anneal Roll | 70 |
| Melt Temp 2 | 416 | Melt Temp 2 | 382 | Amos | | Cooling Roll | |
| Pressure 1 | 1290 | Pressure 1 | 1260 | KW | | | |
| Pressure 2 | 720 | Pressure 2 | 600 | | | | |

TABLE 4

Laminate #4

| | | | | | | | |
|---|---|---|---|---|---|---|---|
| | Gauge | 0.0018 | | Air Gap | | Cost | |
| | Width | 22" | | Emboss Pattern | | 20RA | |
| | Footage | 850 | | CO-EX Block | | BA | |
| | Treat | NONE | | AB 50/50, BAB 10/80/10 | | | |
| | | | | BAB 20/60/20 | | | |
| SCREWS STD | A | 20-100-20 | C NA | CBAD 10/40/40/10 | | | |
| DIE 33" FG | B | 20-150-20 | D NA | CADBDAC | | | |
| | | | | 10/20/10/20/20/20/10 | | | |

| | Ratio | | | | | | |
|---|---|---|---|---|---|---|---|
| Primary Roll fpm | 72 | Tension Pot | 10% | Ext. B rpm | 23 | Ext. C rpm | NA |
| Anneal Roll fpm | 73 1.0 | Taper Pot | 30% | Ext. B amps | 20 | Ext. C amps | NA |
| Cooling Roll fpm | 73--1 | Tension | 2.8% | Ext. A rpm | 35 | Ext. D rpm | NA |
| Winder Nip fpm | 73 1.005 | Vac Box rpm | 27% | Ext. A amps | 42 | Ext. D amps | NA |
| Extruder B | 40% | Extruder A | 60% | Extruder C | 0% | Extruder D | 0% |
| SCC SAM 06150 | 100 | LM 205-10 | 100 | | | | 100 |
| | | | | NA | | NA | |
| Total | 0 | | 0 | | 0 | | 0 |

| Extruder B | | Extruder A | | Extruder C | | Extruder D | |
|---|---|---|---|---|---|---|---|
| Barrel Zone 1 | 330 | Barrel Zone 1 | 340 | Barrel Zone 1 | NA | Barrel Zone 1 | NA |
| Barrel Zone 2 | 350 | Barrel Zone 2 | 370 | Barrel Zone 2 | | Barrel Zone 2 | |
| Barrel Zone 3 | 380 | Barrel Zone 3 | 380 | Barrel Zone 3 | | Barrel Zone 3 | |
| Barrel Zone 4 | 400 | Barrel Zone 4 | 400 | Screen Ch. 1 | | Screen Ch. 1 | |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | | Conn. Pipe 2 | |
| Screen Ch. 3 | | Screen Ch. 3 | | Conn. Pipe 3 | | Conn. Pipe 3 | |
| Valve Zone 1 | | Valve Zone 1 | | Pressure 1 | | Pressure 1 | |
| Conn. Pipe 1 | | Conn. Pipe 1 | | Pressure 2 | | Pressure 2 | |
| Conn. Pipe 2 | 400 | Conn. Pipe 2 | | Melt Temp 1 | | Melt Temp 1 | |
| Die Zone 1 | 420 | Conn. Pipe 3 | 380 | Melt Temp 2 | | Melt Temp 2 | |
| Die Zone 2 | | CO-block 1 | 400 | | | | |
| Die Zone 3 | | CO-block 2 | | | | | |
| Die Zone 4 | | CO-block 3 | | | Treat | | Roll Temp |
| Die Zone 5 | 420 | CO-block 4 | 400 | Top/Bottom | | Chill Roll | 70 |
| Melt Temp 1 | 386 | Melt Temp 1 | 377 | Volts | | Anneal Roll | 70 |
| Melt Temp 2 | 415 | Melt Temp 2 | 384 | Amos | | Cooling Roll | |
| Pressure 1 | 1680 | Pressure 1 | 1350 | KW | | | |
| Pressure 2 | 1030 | Pressure 2 | 680 | | | | |

TABLE 5

Laminate #5

| | | | | | | | |
|---|---|---|---|---|---|---|---|
| | Gauge | 0.0018 | | Air Gap | | Cost | |
| | Width | 22" | | Emboss Pattern | | 20RA | |
| | Footage | 600 | | CO-EX Block | | BA | |
| | Treat | NONE | | AB 50/50, BAB 10/80/10 | | | |
| | | | | BAB 20/60/20 | | | |
| SCREWS STD | A | 20-100-20 | C NA | CBAD 10/40/40/10 | | | |
| DIE 33" FG | B | 20-150-20 | D NA | CADBDAC | | | |
| | | | | 10/20/10/20/20/20/10 | | | |

| | Ratio | | | | | | |
|---|---|---|---|---|---|---|---|
| Primary Roll fpm | 57 | Tension Pot | 10% | Ext. B rpm | 15 | Ext. C rpm | NA |
| Anneal Roll fpm | 58 1.0 | Taper Pot | 30% | Ext. B amps | 15 | Ext. C amps | NA |
| Cooling Roll fpm | 58-1 | Tension | 2.8% | Ext. A rpm | 35 | Ext. D rpm | NA |
| Winder Nip fpm | 58 1.005 | Vac Box rpm | 27% | Ext. A amps | 50 | Ext. D amps | NA |

TABLE 5-continued

Laminate #5

| | | | | | | | | |
|---|---|---|---|---|---|---|---|---|
| Extruder B | 30% | Extruder A | 70% | Extruder C | 0% | Extruder D | | 0% |
| SCC SAM 06150 | 100 | LM 203-10 | 100 | | | | | 100 |
| | | | | NA | | NA | | |
| Total | 0 | | 0 | | 0 | | | 0 |

| Extruder B | | Extruder A | | Extruder C | | Extruder D | |
|---|---|---|---|---|---|---|---|
| Barrel Zone 1 | 330 | Barrel Zone 1 | 340 | Barrel Zone 1 | NA | Barrel Zone 1 | NA |
| Barrel Zone 2 | 350 | Barrel Zone 2 | 370 | Barrel Zone 2 | | Barrel Zone 2 | |
| Barrel Zone 3 | 380 | Barrel Zone 3 | 380 | Barrel Zone 3 | | Barrel Zone 3 | |
| Barrel Zone 4 | 400 | Barrel Zone 4 | 400 | Screen Ch. 1 | | Screen Ch. 1 | |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | | Conn. Pipe 2 | |
| Screen Ch. 3 | | Screen Ch. 3 | | Conn. Pipe 3 | | Conn. Pipe 3 | |
| Valve Zone 1 | | Valve Zone 1 | | Pressure 1 | | Pressure 1 | |
| Conn. Pipe 1 | | Conn. Pipe 1 | | Pressure 2 | | Pressure 2 | |
| Conn. Pipe 2 | 400 | Conn. Pipe 2 | | Melt Temp 1 | | Melt Temp 1 | |
| Die Zone 1 | 420 | Conn. Pipe 3 | 380 | Melt Temp 2 | | Melt Temp 2 | |
| Die Zone 2 | | CO-block 1 | 400 | | | | |
| Die Zone 3 | | CO-block 2 | | | | | |
| Die Zone 4 | | CO-block 3 | | | Treat | | Roll Temp |
| Die Zone 5 | 420 | CO-block 4 | 400 | Top/Bottom | | Chill Roll | 70 |
| Melt Temp 1 | 381 | Melt Temp 1 | 373 | Volts | | Anneal Roll | 70 |
| Melt Temp 2 | 414 | Melt Temp 2 | 387 | Amos | | Cooling Roll | |
| Pressure 1 | 1290 | Pressure 1 | 1290 | KW | | | |
| Pressure 2 | 810 | Pressure 2 | 600 | | | | |

TABLE 6

Laminate #6

| | | | | | | | |
|---|---|---|---|---|---|---|---|
| | Gauge | | 0.0018 | Air Gap | | Cost | |
| | Width | | 22" | Emboss Pattern | | 20RA | |
| | Footage | | 800 | CO-EX Block | | BA | |
| | Treat | | NONE | AB 50/50, BAB 10/80/10 BAB 20/60/20 | | | |
| SCREWS STD | A | 20-100-20 | C NA | CBAD 10/40/40/10 | | | |
| DIE 33" FG | B | 20-150-20 | D NA | CADBDAC 10/20/10/20/20/20/10 | | | |

| | Ratio | | | | | | |
|---|---|---|---|---|---|---|---|
| Primary Roll fpm | 73 | Tension Pot | 10% | Ext. B rpm | 23 | Ext. C rpm | NA |
| Anneal Roll fpm | 73 1.0 | Taper Pot | 30% | Ext. B amps | 20 | Ext. C amps | NA |
| Cooling Roll fpm | — −1 | Tension | 2.8% | Ext. A rpm | 35 | Ext. D rpm | NA |
| Winder Nip fpm | 73 1.005 | Vac Box rpm | 27% | Ext. A amps | 41 | Ext. D amps | NA |

| Extruder B | 40% | Extruder A | 60% | Extruder C | 0% | Extruder D | 0% |
|---|---|---|---|---|---|---|---|
| SCC SAM 06150 | 100 | LM 203–10 | 100 | | | | 100 |
| Total | 0 | | 0 | | 0 | | 0 |

| Extruder B | | Extruder A | | Extruder C | | Extruder D | |
|---|---|---|---|---|---|---|---|
| Barrel Zone 1 | 330 | Barrel Zone 1 | 340 | Barrel Zone 1 | | Barrel Zone 1 | |
| Barrel Zone 2 | 350 | Barrel Zone 2 | 370 | Barrel Zone 2 | | Barrel Zone 2 | |
| Barrel Zone 3 | 380 | Barrel Zone 3 | 380 | Barrel Zone 3 | | Barrel Zone 3 | |
| Barrel Zone 4 | 400 | Barrel Zone 4 | 400 | Screen Ch. 1 | | Screen Ch. 1 | |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | | Conn. Pipe 2 | |
| Screen Ch. 3 | | Screen Ch. 3 | | Conn. Pipe 3 | | Conn. Pipe 3 | |
| Valve Zone 1 | | Valve Zone 1 | | Pressure 1 | | Pressure 1 | |
| Conn. Pipe 1 | | Conn. Pipe 1 | | Pressure 2 | | Pressure 2 | |
| Conn. Pipe 2 | 400 | Conn. Pipe 2 | | Melt Temp 1 | | Melt Temp 1 | |
| Die Zone 1 | 420 | Conn. Pipe 3 | 380 | Melt Temp 2 | | Melt Temp 2 | |

TABLE 6-continued

Laminate #6

| | | | | | | |
|---|---|---|---|---|---|---|
| Die Zone 2 | | CO-block 1 | 400 | | | |
| Die Zone 3 | | CO-block 2 | | | | |
| Die Zone 4 | | CO-block 3 | | | Treat | Roll Temp |
| Die Zone 5 | 420 | CO-block 4 | 380 | Top/Bottom | Chill Roll | 70 |
| Melt Temp 1 | 386 | Melt Temp 1 | 376 | Volts | Anneal Roll | 70 |
| Melt Temp 2 | 417 | Melt Temp 2 | 387 | Amos | Cooling Roll | |
| Pressure 1 | 1530 | Pressure 1 | 1740 | KW | | |
| Pressure 2 | 1000 | Pressure 2 | 990 | | | |

TABLE 7

Laminate #7

| | | | | | | | |
|---|---|---|---|---|---|---|---|
| | Gauge | | 0.001 | | Air Gap | | Cost |
| | Width | | 20" | | Emboss Pattern | | Smooth |
| | Footage | | Small Rolls | | CO-EX Block | | CBAD |
| | Treat | | NONE | | AB 50/50, BAB 10/80/10 | | |
| | | | | | BAB 20/60/20 | | |
| SCREWS STD | A | 20-100-20 | C | DQ-200-DQ | CBAD 10/40/40/10 | | |
| DIE 33" | B | 20-100-20 | D | DQ-200-DQ | CADBDAC | | |
| | FG | | | | 10/20/10/20/20/20/10 | | |

| | Ratio | | | | | | |
|---|---|---|---|---|---|---|---|
| Primary Roll fpm | 160 | Tension Pot | 12% | Ext. B rpm | 20 | Ext. C rpm | 19 |
| Anneal Roll fpm | 162 1.0 | Taper Pot | 30% | Ext. B amps | 41 | Ext. C amps | 3 |
| Cooling Roll fpm | Bypassed | Tension | 3% | Ext. A rpm | 33 | Ext. D rpm | 19 |
| Winder Nip fpm | 169 1.05 | Vac Box rpm | 20% | Ext. A amps | 48 | Ext. D amps | 4 |

| | | | | | | | |
|---|---|---|---|---|---|---|---|
| Extruder B | 30% | Extruder A | 50% | Extruder C | 10% | Extruder D | 10% |
| LM 303.10 | 100 | LM 303.10 | 100 | UB 12 | 100 | UB 12 | 100 |
| Total | 0 | | 0 | | 0 | | 0 |

| Extruder B | | Extruder A | | Extruder C | | Extruder D | |
|---|---|---|---|---|---|---|---|
| Barrel Zone 1 | 340 | Barrel Zone 1 | 340 | Barrel Zone 1 | 370 | Barrel Zone 1 | 370 |
| Barrel Zone 2 | 370 | Barrel Zone 2 | 370 | Barrel Zone 2 | 410 | Barrel Zone 2 | 410 |
| Barrel Zone 3 | 380 | Barrel Zone 3 | 380 | Barrel Zone 3 | 420 | Barrel Zone 3 | 420 |
| Barrel Zone 4 | | Barrel Zone 4 | 400 | Screen Ch. 1 | 430 | Screen Ch. 1 | 430 |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | 430 | Conn. Pipe 2 | 430 |
| Screen Ch. 3 | | Screen Ch. 3 | | Conn. Pipe 3 | | Conn. Pipe 3 | |
| Valve Zone 1 | | Valve Zone 1 | | Pressure 1 | 2690 | Pressure 1 | 2970 |
| Conn. Pipe 1 | | Conn. Pipe 1 | | Pressure 2 | 940 | Pressure 2 | 880 |
| Conn. Pipe 2 | 380 | Conn. Pipe 2 | | Melt Temp 1 | 451 | Melt Temp 1 | 444 |
| Die Zone 1 | 420 | Conn. Pipe 3 | | Melt Temp 2 | 467 | Melt Temp 2 | 455 |
| Die Zone 2 | | CO-block 1 | | | | | |
| Die Zone 3 | | CO-block 2 | | | | | |
| Die Zone 4 | | CO-block 3 | | | Treat | | Roll Temp |
| Die Zone 5 | 420 | CO-block 4 | 380 | Top/Bottom | Chill Roll | | 70 |
| Melt Temp 1 | 364 | Melt Temp 1 | 376 | Volts | Anneal Roll | | 70 |
| Melt Temp 2 | 377 | Melt Temp 2 | 387 | Amos | Cooling Roll | | |
| Pressure 1 | 1430 | Pressure 1 | 1740 | KW | | | |
| Pressure 2 | 910 | Pressure 2 | 990 | | | | |

TABLE 8

Laminate #8

| | | | |
|---|---|---|---|
| Gauge | 0.001 | Air Gap | Cost |
| Width | 20" | Emboss Pattern | Smooth |
| Footage | Small Rolls | CO-EX Block | CBAD |
| Treat | NONE | AB 50/50, BAB 10/80/10 | |
| | | BAB 20/60/20 | |

TABLE 8-continued

| Laminate #8 | | | | | | | | |
|---|---|---|---|---|---|---|---|---|
| SCREWS | STD | A | 20-100-20 | C | DQ-200-DQ | CBAD 10/40/40/10 | | |
| DIE | 33" FG | B | 20-100-20 | D | DQ-200-DQ | CADBDAC 10/20/10/20/20/20/10 | | |

| | | Ratio | | | | | | |
|---|---|---|---|---|---|---|---|---|
| Primary Roll fpm | 121 | | Tension Pot | 50% | Ext. B rpm | 10 | Ext. C rpm | 28 |
| Anneal Roll fpm | 123 | 1.0 | Taper Pot | 30% | Ext. B amps | 36 | Ext. C amps | 3 |
| Cooling Roll fpm | bypassed | | Tension | 8% | Ext. A rpm | 20 | Ext. D rpm | 28 |
| Winder Nip fpm | 130 | 1.05 | Vac Box rpm | 20% | Ext. A amps | 46 | Ext. D amps | 5 |

| Extruder B | | Extruder A | | Extruder C | | Extruder D | |
|---|---|---|---|---|---|---|---|
| | 20% | | 40% | | 20% | | 20% |
| LM 303.10 | 100 | LM 303.10 | 100 | UB 12 | 100 | UB 12 | 100 |
| Total | 0 | | 0 | | 0 | | 0 |

| Extruder B | | Extruder A | | Extruder C | | Extruder D | |
|---|---|---|---|---|---|---|---|
| Barrel Zone 1 | 340 | Barrel Zone 1 | 340 | Barrel Zone 1 | 370 | Barrel Zone 1 | 370 |
| Barrel Zone 2 | 370 | Barrel Zone 2 | 370 | Barrel Zone 2 | 410 | Barrel Zone 2 | 410 |
| Barrel Zone 3 | 380 | Barrel Zone 3 | 380 | Barrel Zone 3 | 420 | Barrel Zone 3 | 420 |
| Barrel Zone 4 | | Barrel Zone 4 | 400 | Screen Ch. 1 | 430 | Screen Ch. 1 | 430 |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | 430 | Conn. Pipe 2 | 430 |
| Screen Ch. 3 | | Screen Ch. 3 | | Conn. Pipe 3 | | Conn. Pipe 3 | |
| Valve Zone 1 | | Valve Zone 1 | | Pressure 1 | 3000 | Pressure 1 | 3370 |
| Conn. Pipe 1 | | Conn. Pipe 1 | | Pressure 2 | 1050 | Pressure 2 | 900 |
| Conn. Pipe 2 | 380 | Conn. Pipe 2 | | Melt Temp 1 | 452 | Melt Temp 1 | 444 |
| Die Zone 1 | 420 | Conn. Pipe 3 | | Melt Temp 2 | 468 | Melt Temp 2 | 462 |
| Die Zone 2 | | CO-block 1 | | | | | |
| Die Zone 3 | | CO-block 2 | | | | | |
| Die Zone 4 | | CO-block 3 | | | Treat | | Roll Temp |
| Die Zone 5 | 420 | CO-block 4 | 380 | Top/Bottom | | Chill Roll | 70 |
| Melt Temp 1 | 358 | Melt Temp 1 | 369 | Volts | | Anneal Roll | 70 |
| Melt Temp 2 | 377 | Melt Temp 2 | 387 | Amos | | Cooling Roll | |
| Pressure 1 | 1090 | Pressure 1 | 1320 | KW | | | |
| Pressure 2 | 600 | Pressure 2 | 740 | | | | |

TABLE 9

| Laminate #9 | | | | | | | | |
|---|---|---|---|---|---|---|---|---|
| | | Gauge | | 5 mil | | Air Gap | | Cost |
| | | Width | | 20" | | Emboss Pattern | | Smooth |
| | | Footage | | Small Rolls | | CO-EX Block | | CBAD |
| | | Treat | | NONE | | AB 50/50, BAB 10/80/10 BAB 20/60/20 | | |
| SCREWS | STD | A | 20-100-20 | C | DQ-200-DQ | CBAD 10/40/40/10 | | |
| DIE | 33" FG | B | 20-100-20 | D | DQ-200-DQ | CADBDAC 10/20/10/20/20/20/10 | | |

| | | Ratio | | | | | | |
|---|---|---|---|---|---|---|---|---|
| Primary Roll fpm | 27 | | Tension Pot | 30% | Ext. B rpm | 20 | Ext. C rpm | 47 |
| Anneal Roll fpm | 27 | 1.0 | Taper Pot | 30% | Ext. B amps | 42 | Ext. C amps | 5 |
| Cooling Roll fpm | bypassed | | Tension | 8% | Ext. A rpm | 13 | Ext. D rpm | 47 |
| Winder Nip fpm | 28 | 1.02 | Vac Box rpm | 20% | Ext. A amps | 40 | Ext. D amps | 5 |

| Extruder B | | Extruder A | | Extruder C | | Extruder D | |
|---|---|---|---|---|---|---|---|
| | 30% | | 20% | | 25% | | 25% |
| LM 303.10 | 100 | LM 303.10 | 100 | UB 12 | 100 | UB 12 | 100 |
| Total | 0 | | 0 | | 0 | | 0 |

TABLE 9-continued

Laminate #9

| Extruder B | | Extruder A | | Extruder C | | Extruder D | |
|---|---|---|---|---|---|---|---|
| Barrel Zone 1 | 340 | Barrel Zone 1 | 340 | Barrel Zone 1 | 370 | Barrel Zone 1 | 370 |
| Barrel Zone 2 | 370 | Barrel Zone 2 | 370 | Barrel Zone 2 | 410 | Barrel Zone 2 | 410 |
| Barrel Zone 3 | 380 | Barrel Zone 3 | 380 | Barrel Zone 3 | 420 | Barrel Zone 3 | 420 |
| Barrel Zone 4 | | Barrel Zone 4 | 400 | Screen Ch. 1 | 430 | Screen Ch. 1 | 430 |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | 430 | Conn. Pipe 2 | 430 |
| Screen Ch. 3 | | Screen Ch. 3 | | Conn. Pipe 3 | | Conn. Pipe 3 | |
| Valve Zone 1 | | Valve Zone 1 | | Pressure 1 | 3590 | Pressure 1 | 3800 |
| Conn. Pipe 1 | | Conn. Pipe 1 | | Pressure 2 | 1360 | Pressure 2 | 1280 |
| Conn. Pipe 2 | 380 | Conn. Pipe 2 | | Melt Temp 1 | 457 | Melt Temp 1 | 450 |
| Die Zone 1 | 420 | Conn. Pipe 3 | | Melt Temp 2 | 470 | Melt Temp 2 | 474 |
| Die Zone 2 | | CO-block 1 | | | | | |
| Die Zone 3 | | CO-block 2 | | | | | |
| Die Zone 4 | | CO-block 3 | | | Treat | | Roll Temp |
| Die Zone 5 | 420 | CO-block 4 | 380 | Top/Bottom | | Chill Roll | 70 |
| Melt Temp 1 | 369 | Melt Temp 1 | 372 | Volts | | Anneal Roll | 70 |
| Melt Temp 2 | 371 | Melt Temp 2 | 387 | Amos | | Cooling Roll | |
| Pressure 1 | 1390 | Pressure 1 | 970 | KW | | | |
| Pressure 2 | 470 | Pressure 2 | 580 | | | | |

TABLE 10

Laminate #10

| | | Gauge | | 5 & 10 mil | | Air Gap | | Cost | |
|---|---|---|---|---|---|---|---|---|---|
| | | Width | | 20" | | Emboss Pattern | | Smooth | |
| | | Footage | | Small Rolls | | CO-EX Block | | CBAD | |
| | | Treat | | NONE | | AB 50/50, BAB 10/80/10 | | | |
| | | | | | | BAB 20/60/20 | | | |
| SCREWS | STD | A | 20-100-20 | C | DQ-200-DQ | CBAD 10/40/40/10 | | | |
| DIE | 33" | B | 20-100-20 | D | DQ-200-DQ | CADBDAC 10/20/10/20/20/20/10 | | | |
| | | FG | | | | | | | |

| | Ratio | | | | | | |
|---|---|---|---|---|---|---|---|
| Primary Roll fpm | 50 | Tension Pot | 12% | Ext. B rpm | 40 | Ext. C rpm | 14 |
| Anneal Roll fpm | 50 1.0 | Taper Pot | 30% | Ext. B amps | | Ext. C amps | |
| Cooling Roll fpm | bypassed | Tension | 4% | Ext. A rpm | 50 | Ext. D rpm | 14 |
| Winder Nip fpm | 52 1.05 | Vac Box rpm | 20% | Ext. A amps | | Ext. D amps | |

| Extruder B | | Extruder A | | Extruder C | | Extruder D | |
|---|---|---|---|---|---|---|---|
| LM 303.10 | 40% 100 | LM 303.10 | 50% 100 | UB 12 | 5% 100 | UB 12 | 5% 100 |
| Total | 0 | | 0 | | 0 | | 0 |

| Extruder B | | Extruder A | | Extruder C | | Extruder D | |
|---|---|---|---|---|---|---|---|
| Barrel Zone 1 | 340 | Barrel Zone 1 | 340 | Barrel Zone 1 | 370 | Barrel Zone 1 | 370 |
| Barrel Zone 2 | 370 | Barrel Zone 2 | 370 | Barrel Zone 2 | 410 | Barrel Zone 2 | 410 |
| Barrel Zone 3 | 380 | Barrel Zone 3 | 380 | Barrel Zone 3 | 420 | Barrel Zone 3 | 420 |
| Barrel Zone 4 | | Barrel Zone 4 | 400 | Screen Ch. 1 | 430 | Screen Ch. 1 | 430 |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | 430 | Conn. Pipe 2 | 430 |
| Screen Ch. 3 | | Screen Ch. 3 | | Conn. Pipe 3 | | Conn. Pipe 3 | |
| Valve Zone 1 | | Valve Zone 1 | | Pressure 1 | 2100 | Pressure 1 | 2300 |
| Conn. Pipe 1 | | Conn. Pipe 1 | | Pressure 2 | 820 | Pressure 2 | 820 |
| Conn. Pipe 2 | | Conn. Pipe 2 | | Melt Temp 1 | 451 | Melt Temp 1 | 444 |
| Die Zone 1 | 420 | Conn. Pipe 3 | | Melt Temp 2 | 470 | Melt Temp 2 | 453 |
| Die Zone 2 | | CO-block 1 | | | | | |
| Die Zone 3 | | CO-block 2 | | | | | |
| Die Zone 4 | | CO-block 3 | | | Treat | | Roll Temp |
| Die Zone 5 | 420 | CO-block 4 | 380 | Top/Bottom | | Chill Roll | 70 |
| Melt Temp 1 | 377 | Melt Temp 1 | 386 | Volts | | Anneal Roll | 70 |
| Melt Temp 2 | 365 | Melt Temp 2 | 386 | Amos | | Cooling Roll | |

TABLE 10-continued

Laminate #10

| | | | | |
|---|---|---|---|---|
| Pressure 1 | 2000 | Pressure 1 | 2020 | KW |
| Pressure 2 | 1160 | Pressure 2 | 1110 | |

TABLE 11

Laminate #11

| | | | | | | | | |
|---|---|---|---|---|---|---|---|---|
| | | Gauge | | 5 & 10 mil | Air Gap | | Cost | |
| | | Width | | 20" | Emboss Pattern | | Smooth | |
| | | Footage | | Small Rolls | CO-EX Block | | CBAD | |
| | | Treat | | NONE | AB 50/50, BAB 10/80/10 | | | |
| | | | | | BAB 20/60/20 | | | |
| SCREWS | STD | A | 20-100-20 | C DQ-200-DQ | CBAD 10/40/40/10 | | | |
| DIE | 33" | B | 20-100-20 | D DQ-200-DQ | CADBDAC | | | |
| | FG | | | | 10/20/10/20/20/20/10 | | | |

| | Ratio | | | | | | | |
|---|---|---|---|---|---|---|---|---|
| Primary Roll fpm | 38 | Tension Pot | 12% | Ext. B rpm | 21 | Ext. C rpm | 36 |
| Anneal Roll fpm | 39 1.0 | Taper Pot | 30% | Ext. B amps | 44 | Ext. C amps | 4 |
| Cooling Roll fpm | bypassed | Tension | 4% | Ext. A rpm | 40 | Ext. D rpm | 36 |
| Winder Nip fpm | 1.005 | Vac Box rpm | 20% | Ext. A amps | 51 | Ext. D amps | 5 |

| Extruder B | | Extruder A | | Extruder C | | Extruder D | |
|---|---|---|---|---|---|---|---|
| LM 303.10 | 20% | LM 303.10 | 50% | UB 12 | 15% | UB 12 | 15% |
| Total | 100 0 | | 100 0 | | 100 0 | | 100 0 |

| Extruder B | | Extruder A | | Extruder C | | Extruder D | |
|---|---|---|---|---|---|---|---|
| Barrel Zone 1 | 340 | Barrel Zone 1 | 340 | Barrel Zone 1 | 370 | Barrel Zone 1 | 370 |
| Barrel Zone 2 | 370 | Barrel Zone 2 | 370 | Barrel Zone 2 | 410 | Barrel Zone 2 | 410 |
| Barrel Zone 3 | 380 | Barrel Zone 3 | 380 | Barrel Zone 3 | 420 | Barrel Zone 3 | 420 |
| Barrel Zone 4 | | Barrel Zone 4 | 400 | Screen Ch. 1 | 430 | Screen Ch. 1 | 430 |
| Barrel Zone 5 | | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | 430 | Conn. Pipe 2 | 430 |
| Screen Ch. 3 | | Screen Ch. 3 | | Conn. Pipe 3 | | Conn. Pipe 3 | |
| Valve Zone 1 | | Valve Zone 1 | | Pressure 1 | 3250 | Pressure 1 | 3370 |
| Conn. Pipe 1 | | Conn. Pipe 1 | | Pressure 2 | 1310 | Pressure 2 | 1270 |
| Conn. Pipe 2 | 380 | Conn. Pipe 2 | | Melt Temp 1 | 453 | Melt Temp 1 | 446 |
| Die Zone 1 | 420 | Conn. Pipe 3 | | Melt Temp 2 | 469 | Melt Temp 2 | 469 |
| Die Zone 2 | | CO-block 1 | | | | | |
| Die Zone 3 | | CO-block 2 | | | | | |
| Die Zone 4 | | CO-block 3 | | | Treat | | Roll Temp |
| Die Zone 5 | 420 | CO-block 4 | 380 | Top/Bottom | | Chill Roll | 70 |
| Melt Temp 1 | 367 | Melt Temp 1 | 381 | Volts | | Anneal Roll | |
| Melt Temp 2 | 372 | Melt Temp 2 | 387 | Amos | | Cooling Roll | |
| Pressure 1 | 1630 | Pressure 1 | 2000 | KW | | | |
| Pressure 2 | 1030 | Pressure 2 | 1130 | | | | |

TABLE 12

Laminate #12

| | | | | | | | |
|---|---|---|---|---|---|---|---|
| | | Gauge | | 5, 10 & 15 mil | Air Gap | | Cost |
| | | Width | | 31 | Emboss Pattern | | Smooth |
| | | Footage | | Slabs | CO-EX Block | | CBAD |
| | | Treat | | NONE | AB 50/50, BAB 10/80/10 | | |
| | | | | | BAB 20/60/20 | | |
| SCREWS | STD | A | 20-100-20 | C DQ-200-DQ | CBAD 10/40/40/10 | | |
| DIE | 33" | B | 20-100-20 | D DQ-200-DQ | CADBDAC | | |
| | FG | | | | 10/20/10/20/20/20/10 | | |

TABLE 12-continued

Laminate #12

| | Ratio | | | | | | |
|---|---|---|---|---|---|---|---|
| Primary Roll fpm | 54 | Tension Pot | 20% | Ext. B rpm | 40 | Ext. C rpm | 10 |
| Anneal Roll fpm | 1 | Taper Pot | 30% | Ext. B amps | 40 | Ext. C amps | |
| Cooling Roll fpm | bypassed | Tension | 5% | Ext. A rpm | 40 | Ext. D rpm | 10 |
| Winder Nip fpm | 1.02 | Vac Box rpm | 20% | Ext. A amps | 42 | Ext. D amps | |

| Extruder B | % | Extruder A | % | Extruder C | % | Extruder D | % |
|---|---|---|---|---|---|---|---|
| LM 202.10 | 100 | LM 202.10 | 100 | SURLYN 1702 | 100 | SURLYN 1702 | 100 |
| Total | 0 | | 0 | | 0 | | 0 |

| Extruder B | | Extruder A | | Extruder C | | Extruder D | |
|---|---|---|---|---|---|---|---|
| Barrel Zone 1 | 340 | Barrel Zone 1 | 340 | Barrel Zone 1 | 325 | Barrel Zone 1 | 325 |
| Barrel Zone 2 | 370 | Barrel Zone 2 | 370 | Barrel Zone 2 | 350 | Barrel Zone 2 | 350 |
| Barrel Zone 3 | 380 | Barrel Zone 3 | 380 | Barrel Zone 3 | 380 | Barrel Zone 3 | 380 |
| Barrel Zone 4 | 410 | Barrel Zone 4 | 400 | Screen Ch. 1 | 400 | Screen Ch. 1 | 400 |
| Barrel Zone 5 | 400 | Barrel Zone 5 | | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | 400 | Conn. Pipe 2 | 400 |
| Screen Ch. 3 | | Screen Ch. 3 | | Conn. Pipe 3 | | Conn. Pipe 3 | |
| Valve Zone 1 | | Valve Zone 1 | | Pressure 1 | 350 | Pressure 1 | 390 |
| Conn. Pipe 1 | | Conn. Pipe 1 | | Pressure 2 | 270 | Pressure 2 | 270 |
| Conn. Pipe 2 | | Conn. Pipe 2 | | Melt Temp 1 | 418 | Melt Temp 1 | 414 |
| Die Zone 1 | | Conn. Pipe 3 | | Melt Temp 2 | 439 | Melt Temp 2 | 424 |
| Die Zone 2 | | CO-block 1 | | | | | |
| Die Zone 3 | | CO-block 2 | | | | | |
| Die Zone 4 | | CO-block 3 | | | Treat | | Roll Temp |
| Die Zone 5 | 380 | CO-block 4 | 380 | Top/Bottom | | Chill Roll | 70 |
| Melt Temp 1 | 378 | Melt Temp 1 | 380 | Volts | | Anneal Roll | 70 |
| Melt Temp 2 | 377 | Melt Temp 2 | 386 | Amos | | Cooling Roll | |
| Pressure 1 | 1470 | Pressure 1 | 1600 | KW | | | |
| Pressure 2 | 720 | Pressure 2 | 880 | | | | |

TABLE 13

Laminate #13

| | | | | | | | |
|---|---|---|---|---|---|---|---|
| | | Gauge | 5 mil | | Air Gap | | Cost |
| | | Width | 31 | | Emboss Pattern | | Smooth |
| | | Footage | SLABS | | CO-EX Block | | CBAD |
| | | Treat | NONE | | AB 50/50, BAB 10/80/10 | | |
| | | | | | BAB 20/60/20 | | |
| SCREWS | STD | A | 20-100-20 | C | DQ-200-DQ | CBAD 10/40/40/10 | |
| DIE | 33" | B | 20-100-20 | D | DQ-200-DQ | CADBDAC | |
| | FG | | | | | 10/20/10/20/20/10 | |

| | Ratio | | | | | | |
|---|---|---|---|---|---|---|---|
| Primary Roll fpm | 80 | Tension Pot | | Ext. B rpm | 75 | Ext. C rpm | 10 |
| Anneal Roll fpm | | Taper Pot | | Ext. B amps | 67 | Ext. C amps | |
| Cooling Roll fpm | | Tension | | Ext. A rpm | 75 | Ext. D rpm | 10 |
| Winder Nip fpm | | Vac Box rpm | | Ext. A amps | 72 | Ext. D amps | |

| Extruder B | % | Extruder A | % | Extruder C | % | Extruder D | % |
|---|---|---|---|---|---|---|---|
| ESTANE 58680 | 100 | ESTANE 58680 | 100 | SURLYN 1702 | 100 | SURLYN 1702 | 100 |
| Total | 0 | | 0 | | 0 | | 0 |

| Extruder B | | Extruder A | | Extruder C | | Extruder D | |
|---|---|---|---|---|---|---|---|
| Barrel Zone 1 | 390 | Barrel Zone 1 | 390 | Barrel Zone 1 | 325 | Barrel Zone 1 | 325 |
| Barrel Zone 2 | 400 | Barrel Zone 2 | 400 | Barrel Zone 2 | 350 | Barrel Zone 2 | 350 |
| Barrel Zone 3 | 410 | Barrel Zone 3 | 410 | Barrel Zone 3 | 380 | Barrel Zone 3 | 380 |
| Barrel Zone 4 | 410 | Barrel Zone 4 | 410 | Screen Ch. 1 | 400 | Screen Ch. 1 | 400 |
| Barrel Zone 5 | 400 | Barrel Zone 5 | 400 | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | 400 | Conn. Pipe 2 | 400 |
| Screen Ch. 3 | | Screen Ch. 3 | | Conn. Pipe 3 | | Conn. Pipe 3 | |

TABLE 13-continued

Laminate #13

| | | | | | | | |
|---|---|---|---|---|---|---|---|
| Valve Zone 1 | | Valve Zone 1 | | Pressure 1 | 300 | Pressure 1 | 350 |
| Conn. Pipe 1 | | Conn. Pipe 1 | | Pressure 2 | 250 | Pressure 2 | 80 |
| Conn. Pipe 2 | 400 | Conn. Pipe 2 | | Melt Temp 1 | 424 | Melt Temp 1 | 420 |
| Die Zone 1 | 420 | Conn. Pipe 3 | | Melt Temp 2 | 464 | Melt Temp 2 | 456 |
| Die Zone 2 | | CO-block 1 | | | | | |
| Die Zone 3 | | CO-block 2 | | | | | |
| Die Zone 4 | | CO-block 3 | | | Treat | | Roll Temp |
| Die Zone 5 | 420 | CO-block 4 | 400 | Top/Bottom | | Chill Roll | 70 |
| Melt Temp 1 | 407 | Melt Temp 1 | 411 | Volts | | Anneal Roll | 70 |
| Melt Temp 2 | 391 | Melt Temp 2 | 429 | Amos | | Cooling Roll | |
| Pressure 1 | 1500 | Pressure 1 | 1600 | KW | | | |
| Pressure 2 | 510 | Pressure 2 | 600 | | | | |

TABLE 14

Laminate #14

| | | | | | | | |
|---|---|---|---|---|---|---|---|
| | | Gauge | 5, 10, & 15 mil | Air Gap | | Cost | |
| | | Width | 31 | Emboss Pattern | | Smooth | |
| | | Footage | SLABS | CO-EX Block | | CBAD | |
| | | Treat | NONE | AB 50/50, BAB 10/80/10 BAB 20/60/20 | | | |
| SCREWS | STD | A 20-100-20 | C DQ-200-DQ | CBAD 10/40/40/10 | | | |
| DIE | 3.3" FG | B 20-100-20 | D DQ-200-DQ | CADBDAC 10/20/10/20/20/20/10 | | | |

| | Ratio | | | | | | |
|---|---|---|---|---|---|---|---|
| Primary Roll fpm | 80 | Tension Pot | 50 | Ext. B rpm | 7.5 | Ext. C rpm | 10 |
| Anneal Roll fpm | 1 | Taper Pot | 30 | Ext. B amps | | Ext. C amps | |
| Cooling Roll fpm | bypassed | Tension | 11 | Ext. A rpm | 7.5 | Ext. D rpm | 10 |
| Winder Nip fpm | 1.05 | Vac Box rpm | 21 | Ext. A amps | | Ext. D amps | |

| Extruder B | % | Extruder A | % | Extruder C | % | Extruder D | % |
|---|---|---|---|---|---|---|---|
| PEBAX 2533 | 100 | PEBAX 2533 | 100 | SURLYN 1702 | 100 | SURLYN 1702 | 100 |
| Total | 0 | | 0 | | 0 | | 0 |

| Extruder B | | Extruder A | | Extruder C | | Extruder D | |
|---|---|---|---|---|---|---|---|
| Barrel Zone 1 | 320 | Barrel Zone 1 | 320 | Barrel Zone 1 | 325 | Barrel Zone 1 | 325 |
| Barrel Zone 2 | 350 | Barrel Zone 2 | 350 | Barrel Zone 2 | 350 | Barrel Zone 2 | 350 |
| Barrel Zone 3 | 380 | Barrel Zone 3 | 380 | Barrel Zone 3 | 380 | Barrel Zone 3 | 380 |
| Barrel Zone 4 | 400 | Barrel Zone 4 | 400 | Screen Ch. 1 | 400 | Screen Ch. 1 | 400 |
| Barrel Zone 5 | 400 | Barrel Zone 5 | 400 | Valve Zone 1 | | Valve Zone 1 | |
| Screen Ch. 1 | | Screen Ch. 1 | | Conn. Pipe 1 | | Conn. Pipe 1 | |
| Screen Ch. 2 | | Screen Ch. 2 | | Conn. Pipe 2 | 400 | Conn. Pipe 2 | 400 |
| Screen Ch. 3 | | Screen Ch. 3 | | Conn. Pipe 3 | | Conn. Pipe 3 | |
| Valve Zone 1 | | Valve Zone 1 | | Pressure 1 | 300 | Pressure 1 | 350 |
| Conn. Pipe 1 | | Conn. Pipe 1 | | Pressure 2 | 250 | Pressure 2 | 80 |
| Conn. Pipe 2 | 400 | Conn. Pipe 2 | | Melt Temp 1 | 424 | Melt Temp 1 | 420 |
| Die Zone 1 | 420 | Conn. Pipe 3 | | Melt Temp 2 | 464 | Melt Temp 2 | 456 |
| Die Zone 2 | | CO-block 1 | | | | | |
| Die Zone 3 | | CO-block 2 | | | | | |
| Die Zone 4 | | CO-block 3 | | | Treat | | Roll Temp |
| Die Zone 5 | 420 | CO-block 4 | 400 | Top/Bottom | | Chill Roll | 70 |
| Melt Temp 1 | 394 | Melt Temp 1 | 397 | Volts | | Anneal Roll | 70 |
| Melt Temp 2 | 384 | Melt Temp 2 | 408 | Amos | | Cooling Roll | |
| Pressure 1 | 1090 | Pressure 1 | 1170 | KW | | | |
| Pressure 2 | 550 | Pressure 2 | 650 | | | | |

Mocon Test Procedure For Water Vapor Transmission Rate (WVTR)

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The testing device is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:
WVTR: The calculation of the WVTR uses the formula:

$$WVTR = F\rho_{sat}(T)RH/A\rho_{sat}(T)(1-RH)$$

where:
F=The flow of water vapor in cc/min.,
$\rho_{sat}(T)$=The density of water in saturated air at temperature T,
RH=The relative humidity at specified locations in the cell,
A=The cross sectional area of the cell, and,
$p_{sat}(T)$=The saturation vapor pressure of water vapor at temperature T.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A breathable, elastic, film laminate comprising:
    at least one layer of an inherently breathable, elastic polymer film comprising a thermoplastic polymer grafted to an elastomer, wherein the thermoplastic polymer contains maleic anhydride and the maleic anhydride couples the thermoplastic polymer to the elastomer;
    wherein the at least one layer of the elastic polymer film is between at least two film layers of polyolefin-based plastic polymer wherein at least one film layer is filled with about 50% to about 70% by weight of a non-thermoplastic filler, wherein the at least one layer of an inherently breathable, elastic polymer film retracts and the at least one film filled layer of polyolefin-based plastic polymer buckles so the elastic polymer film is partially delaminated from the at least one film layer of the polyolefin-based plastic polymer.

2. The laminate of claim 1, wherein the laminate comprises between about 10% and about 90% elastic polymer.

3. The laminate of claim 1, wherein the laminate comprises between about 20% and about 80% elastic polymer.

4. The laminate of claim 1, wherein the laminate comprises between about 30% and about 70% elastic polymer.

5. The laminate of claim 1, wherein the laminate comprises between about 10% and about 90% filled plastic polymer.

6. The laminate of claim 1, wherein the laminate comprises between about 20% and about 80% filled plastic polymer.

7. The laminate of claim 1, wherein the laminate comprises between about 30% and about 70% filled plastic polymer.

8. The laminate of claim 1, wherein the thermoplastic polymer grafted elastomer comprises polypropylene grafted to a thermoplastic polyurethane.

9. The laminate of claim 8, wherein the grafting is mediated with an amine.

10. The laminate of claim 9, wherein the amine includes a di-amine.

11. The laminate of claim 1, wherein the thermoplastic polymer grafted elastomer comprises polyethylene grafted to a thermoplastic polyurethane.

12. The laminate of claim 1, wherein the thermoplastic polymer grafted elastomer comprises between about 1% and about 70% polyolefin.

13. The laminate of claim 1, wherein the thermoplastic polymer grafted elastomer comprises between about 5% and about 50% polyolefin.

14. The laminate of claim 1, wherein the plastic polymer comprises linear low density polyethylene.

15. The laminate of claim 1, wherein the filler comprises calcium carbonate.

16. The laminate of claim 1, further comprising a tie layer between a layer of the elastic polymer film and a layer of the plastic polymer.

17. The laminate of claim 1, further comprising a facing layer bonded to an outer layer of the laminate.

18. The laminate of claim 17, wherein the facing layer comprises a nonwoven web.

19. The laminate of claim 1, having a water vapor transmission rate of between about 1,000 and about 20,000 grams/m$^2$-24 hours.

20. The laminate of claim 1, having a water vapor transmission rate of between about 3,000 and about 15,000 grams/m$^2$-24 hours.

21. An absorbent article comprising the laminate of claim 1.

22. The absorbent article of claim 21, wherein an outer cover of the article comprises the laminate.

23. A breathable, elastic, film laminate, comprising:
    at least one layer of an inherently breathable, elastic polymer film including a thermoplastic polymer grafted to an elastomer, wherein the thermoplastic polymer contains maleic anhydride and the maleic anhydride couples the thermoplastic polymer to the elastomer; and
    at least two film layers of a polyolefin-based plastic polymer wherein at least one film layer is filled with about 50% to about 70% by weight of a non-thermoplastic filler, with alternating layers of the elastic polymer film and the plastic polymer, wherein the at least one layer of an inherently breathable, elastic polymer film retracts and the at least one filled film layer of the polyolefin-based plastic polymer buckles so the laminate has a lofty structure and the elastic polymer film is partially delaminated from the at least one filled film layer of the polyolefin-based plastic polymer.

24. The laminate of claim 23, comprising at least two layers of the elastic polymer film and at least three layers of the plastic polymer.

25. The laminate of claim 23, comprising at least three layers of the elastic polymer film and at least four layers of the plastic polymer.

26. An absorbent article comprising the laminate of claim 23.

27. The absorbent article of claim 26, wherein an outer cover of the article comprises the laminate.

* * * * *